United States Patent
Bess et al.

(10) Patent No.: US 9,526,553 B2
(45) Date of Patent: Dec. 27, 2016

(54) SCREW INSERTION INSTRUMENT

(71) Applicant: K2M, Inc., Leesburg, VA (US)

(72) Inventors: Robert Shay Bess, Castle Rock, CO (US); Theo Choi, Arlington, VA (US)

(73) Assignee: K2M, Inc., Leesburg, VA (US)

( * ) Notice: Subject to any disclaimer, the term of this patent is extended or adjusted under 35 U.S.C. 154(b) by 196 days.

(21) Appl. No.: 14/245,346

(22) Filed: Apr. 4, 2014

(65) Prior Publication Data

US 2015/0282855 A1 Oct. 8, 2015

(51) Int. Cl.
*A61B 17/70* (2006.01)
*A61B 17/88* (2006.01)

(52) U.S. Cl.
CPC ....... *A61B 17/8875* (2013.01); *A61B 17/7082* (2013.01)

(58) Field of Classification Search
CPC ........ A61B 17/7074–17/7082; A61B 17/7091; A61F 2/4611
USPC ......................................... 606/86 A, 99, 104
See application file for complete search history.

(56) References Cited

U.S. PATENT DOCUMENTS

| | | | |
|---|---|---|---|
| 2,248,054 A * | 7/1941 | Becker ............................ | 81/457 |
| 5,423,819 A | 6/1995 | Small et al. | |
| 5,484,440 A | 1/1996 | Allard | |
| 5,649,931 A * | 7/1997 | Bryant et al. ................. | 606/104 |
| 5,836,430 A * | 11/1998 | Vasudeva ..................... | 192/43.2 |
| 5,885,299 A * | 3/1999 | Winslow et al. ............... | 606/99 |
| 5,941,885 A * | 8/1999 | Jackson ......................... | 606/104 |
| 5,946,988 A | 9/1999 | Metz-Stavenhagen | |
| 6,132,435 A * | 10/2000 | Young ........................... | 606/104 |
| 6,189,422 B1 | 2/2001 | Stihl | |
| 6,299,616 B1 * | 10/2001 | Beger .......................... | 606/86 R |
| 6,827,722 B1 * | 12/2004 | Schoenefeld ................. | 606/104 |
| 6,974,466 B2 * | 12/2005 | Ahmed et al. ................ | 606/140 |
| 7,181,997 B1 * | 2/2007 | Rinner et al. .................. | 81/58.4 |
| 7,559,930 B2 * | 7/2009 | Allard et al. ............... | 606/86 A |
| 7,572,264 B2 | 8/2009 | Null et al. | |
| 7,600,451 B2 * | 10/2009 | Lechot et al. .................... | 81/62 |
| 7,697,129 B2 | 4/2010 | Haller et al. | |
| 7,758,584 B2 | 7/2010 | Bankoski et al. | |
| 7,947,048 B2 | 5/2011 | Doll et al. | |
| 8,002,798 B2 | 8/2011 | Chin et al. | |
| 8,062,340 B2 | 11/2011 | Berrevoets et al. | |

(Continued)

FOREIGN PATENT DOCUMENTS

EP 1946711 A1 7/2008
WO 2011043799 A1 4/2011

OTHER PUBLICATIONS

Extended European Search Report dated Oct. 1, 2015.

*Primary Examiner* — Eduardo C Robert
*Assistant Examiner* — Michelle C Eckman
(74) *Attorney, Agent, or Firm* — Carter, DeLuca, Farrell & Schmidt, LLP

(57) ABSTRACT

An instrument for selectively coupling with a pedicle screw is disclosed. The instrument includes an inner shaft, wherein the distal tip is configured to engage a pedicle screw and the proximal end configured to be selectively engaged with a knob, and a knob assembly configured to advance over the inner shaft, wherein the distal end is configured to engage the tulip of the pedicle screw and the proximal end is configured to selectively engage the inner shaft. A method for selectively coupling the instrument to a pedicle screw is also disclosed.

20 Claims, 20 Drawing Sheets

(56) References Cited

U.S. PATENT DOCUMENTS

| | | | |
|---|---|---|---|
| 8,100,916 B2 | 1/2012 | Kumar et al. | |
| 8,105,328 B2* | 1/2012 | Protopsaltis | 606/86 A |
| 8,206,394 B2* | 6/2012 | Stad et al. | 606/86 A |
| 8,216,243 B2* | 7/2012 | Yevmenenko et al. | 606/99 |
| 8,231,635 B2 | 7/2012 | Sharifi-Mehr et al. | |
| 8,273,089 B2 | 9/2012 | Jackson | |
| 8,343,165 B2 | 1/2013 | Berrevoets | |
| 8,394,108 B2* | 3/2013 | McLean et al. | 606/104 |
| 8,439,922 B1* | 5/2013 | Arnold et al. | 606/86 A |
| 8,460,307 B2 | 6/2013 | Saidha et al. | |
| 8,512,344 B2 | 8/2013 | Hoffman et al. | |
| 8,512,383 B2* | 8/2013 | McLean | 606/279 |
| 8,585,705 B2* | 11/2013 | Richelsoph et al. | 606/86 A |
| 8,591,515 B2* | 11/2013 | Jackson | 606/86 A |
| 8,747,411 B2 | 6/2014 | Mitchell | |
| 8,784,431 B1* | 7/2014 | Harder et al. | 606/104 |
| 8,876,869 B1* | 11/2014 | Schafer et al. | 606/278 |
| 8,936,626 B1* | 1/2015 | Tohmeh | A61B 17/1615 606/279 |
| 8,986,349 B1* | 3/2015 | German et al. | 606/279 |
| 9,101,416 B2* | 8/2015 | Dunbar et al. | A61B 17/70 |
| 2003/0236529 A1* | 12/2003 | Shluzas et al. | 606/105 |
| 2004/0138662 A1 | 7/2004 | Landry et al. | |
| 2004/0267275 A1* | 12/2004 | Cournoyer et al. | 606/99 |
| 2005/0033307 A1* | 2/2005 | Cook et al. | 606/104 |
| 2005/0228400 A1* | 10/2005 | Chao et al. | 606/104 |
| 2006/0069391 A1* | 3/2006 | Jackson | 606/62 |
| 2006/0074418 A1* | 4/2006 | Jackson | 606/61 |
| 2006/0111712 A1* | 5/2006 | Jackson | 606/61 |
| 2007/0043378 A1* | 2/2007 | Kumar et al. | 606/104 |
| 2007/0088363 A1* | 4/2007 | Rezach | 606/99 |
| 2007/0270880 A1* | 11/2007 | Lindemann et al. | 606/104 |
| 2008/0045970 A1* | 2/2008 | Saidha et al. | 606/104 |
| 2008/0172062 A1* | 7/2008 | Donahue et al. | 606/104 |
| 2008/0200918 A1* | 8/2008 | Spitler et al. | 606/104 |
| 2008/0221583 A1* | 9/2008 | Sharifi-Mehr et al. | 606/104 |
| 2008/0243133 A1* | 10/2008 | Heinz | 606/104 |
| 2008/0243190 A1* | 10/2008 | Dziedzic et al. | 606/278 |
| 2009/0157125 A1* | 6/2009 | Hoffman et al. | 606/86 A |
| 2009/0163963 A1* | 6/2009 | Berrevoets | 606/86 A |
| 2009/0228053 A1* | 9/2009 | Kolb et al. | 606/86 A |
| 2009/0234395 A1* | 9/2009 | Hoffman et al. | 606/86 A |
| 2009/0264895 A1* | 10/2009 | Gasperut et al. | 606/104 |
| 2009/0264896 A1* | 10/2009 | Biedermann et al. | 606/104 |
| 2009/0275954 A1* | 11/2009 | Phan et al. | 606/104 |
| 2010/0211115 A1* | 8/2010 | Tyber et al. | 606/305 |
| 2010/0298838 A1 | 11/2010 | Walters | |
| 2010/0312279 A1* | 12/2010 | Gephart et al. | 606/264 |
| 2010/0331897 A1* | 12/2010 | Lindner | 606/305 |
| 2011/0046683 A1* | 2/2011 | Biedermann et al. | 606/305 |
| 2011/0245839 A1* | 10/2011 | Lower | 606/104 |
| 2011/0245881 A1* | 10/2011 | Mitchell | 606/304 |
| 2011/0251597 A1* | 10/2011 | Bharadwaj et al. | 606/1 |
| 2011/0313464 A1* | 12/2011 | McLean | 606/279 |
| 2011/0313477 A1* | 12/2011 | McLean et al. | 606/86 A |
| 2012/0031792 A1* | 2/2012 | Petit | 206/438 |
| 2012/0109126 A1* | 5/2012 | Steele et al. | 606/53 |
| 2012/0123431 A1* | 5/2012 | Robinson | 606/104 |
| 2012/0191094 A1* | 7/2012 | Alain et al. | 606/80 |
| 2012/0203287 A1 | 8/2012 | Arambula et al. | |
| 2012/0203288 A1* | 8/2012 | Lange et al. | 606/305 |
| 2012/0253355 A1* | 10/2012 | Murray | A61B 17/8888 606/104 |
| 2012/0253402 A1* | 10/2012 | McLean | 606/264 |
| 2012/0323278 A1* | 12/2012 | Tsuang et al. | 606/264 |
| 2013/0012954 A1* | 1/2013 | Paroth et al. | 606/104 |
| 2013/0012999 A1* | 1/2013 | Petit | 606/279 |
| 2013/0018428 A1* | 1/2013 | Harper et al. | 606/305 |
| 2013/0110124 A1* | 5/2013 | Gleason et al. | 606/104 |
| 2013/0144350 A1* | 6/2013 | Yoko | A61B 17/1764 606/86 R |
| 2013/0150864 A1* | 6/2013 | Marik et al. | 606/104 |
| 2013/0282019 A1* | 10/2013 | Bouliane | A61B 17/7082 606/104 |
| 2014/0018816 A1* | 1/2014 | Fenn et al. | 606/104 |
| 2014/0052187 A1* | 2/2014 | McBride et al. | 606/264 |
| 2014/0100583 A1* | 4/2014 | Butler et al. | 606/104 |
| 2014/0100616 A1* | 4/2014 | Shipp | A61B 17/7082 606/86 A |
| 2014/0107708 A1* | 4/2014 | Biedermann et al. | 606/278 |
| 2014/0249532 A1* | 9/2014 | Biedermann et al. | 606/80 |
| 2014/0257408 A1* | 9/2014 | Trieu et al. | 606/301 |
| 2014/0276892 A1* | 9/2014 | Pakzaban et al. | 606/104 |
| 2014/0277137 A1* | 9/2014 | Stad et al. | 606/246 |
| 2014/0277164 A1* | 9/2014 | Ramsay et al. | 606/279 |
| 2014/0277195 A1* | 9/2014 | McBride | 606/86 A |
| 2014/0277200 A1* | 9/2014 | Parker et al. | 606/86 A |
| 2014/0288567 A1* | 9/2014 | Kroll | 606/104 |
| 2014/0324062 A1* | 10/2014 | Heuer et al. | 606/104 |
| 2014/0336709 A1* | 11/2014 | Avidano et al. | 606/271 |
| 2014/0358186 A1* | 12/2014 | Frock et al. | 606/86 A |
| 2014/0371756 A1* | 12/2014 | Marigowda | 606/104 |
| 2015/0039035 A1* | 2/2015 | Kruger | 606/264 |
| 2015/0066042 A1* | 3/2015 | Cummins et al. | 606/104 |
| 2015/0066084 A1* | 3/2015 | Petit | 606/246 |
| 2015/0066089 A1* | 3/2015 | Nelson et al. | 606/265 |
| 2015/0073423 A1* | 3/2015 | Hoefer et al. | 606/94 |
| 2015/0094781 A1* | 4/2015 | Paroth et al. | 606/86 R |
| 2015/0100094 A1* | 4/2015 | Milz et al. | 606/280 |
| 2015/0105831 A1* | 4/2015 | Yim et al. | 606/86 A |
| 2015/0112397 A1* | 4/2015 | Petit | 606/86 A |
| 2015/0142067 A1* | 5/2015 | Bess et al. | 606/86 A |
| 2015/0148849 A1* | 5/2015 | Abidin | A61B 17/7091 606/279 |
| 2015/0182265 A1* | 7/2015 | Biedermann et al. | A61B 17/7085 |
| 2015/0201985 A1* | 7/2015 | Rampersaud et al. | A61B 17/8875 |
| 2015/0201987 A1* | 7/2015 | Lemoine et al. | A61B 17/8891 |
| 2015/0250521 A1* | 9/2015 | Poker et al. | A61B 17/8875 |
| 2015/0257797 A1* | 9/2015 | Biedermann et al. | A61B 17/7082 |
| 2015/0257798 A1* | 9/2015 | Biedermann et al. | A61B 17/7082 |
| 2015/0265315 A1* | 9/2015 | Sims et al. | A61B 17/70 |
| 2015/0272649 A1* | 10/2015 | Lewis et al. | A61B 17/8875 |

\* cited by examiner

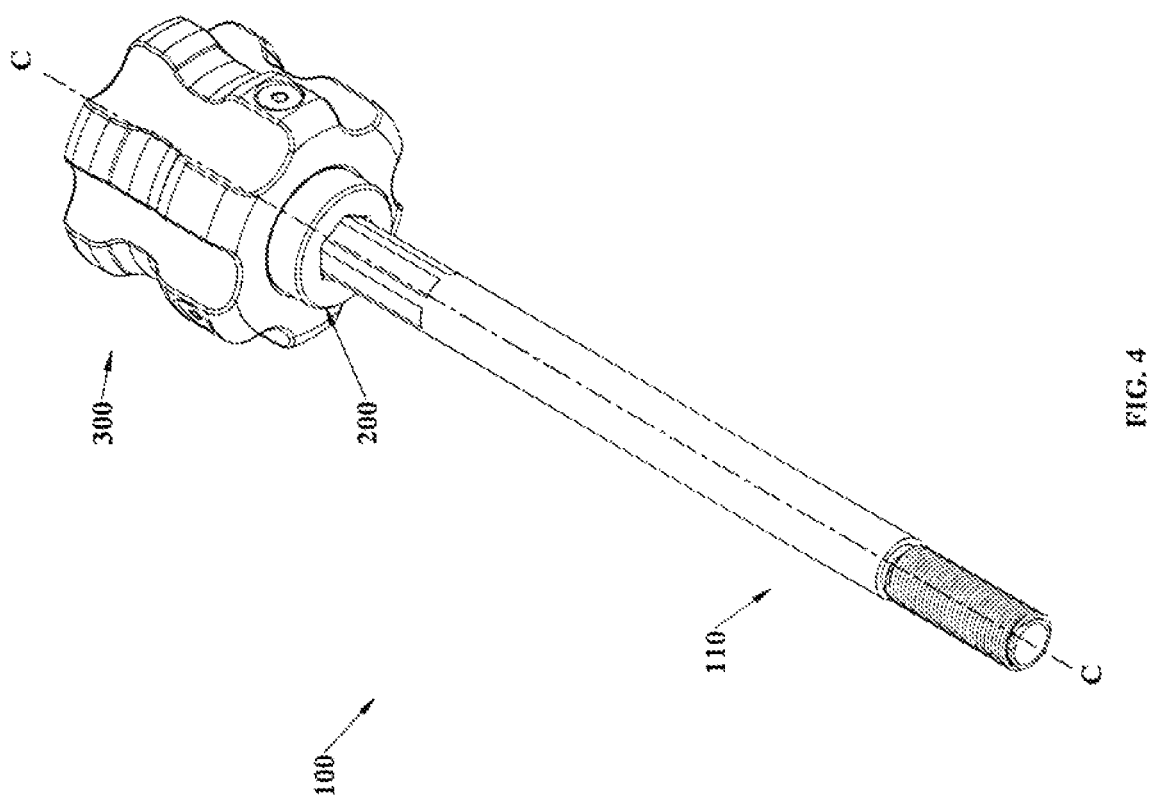

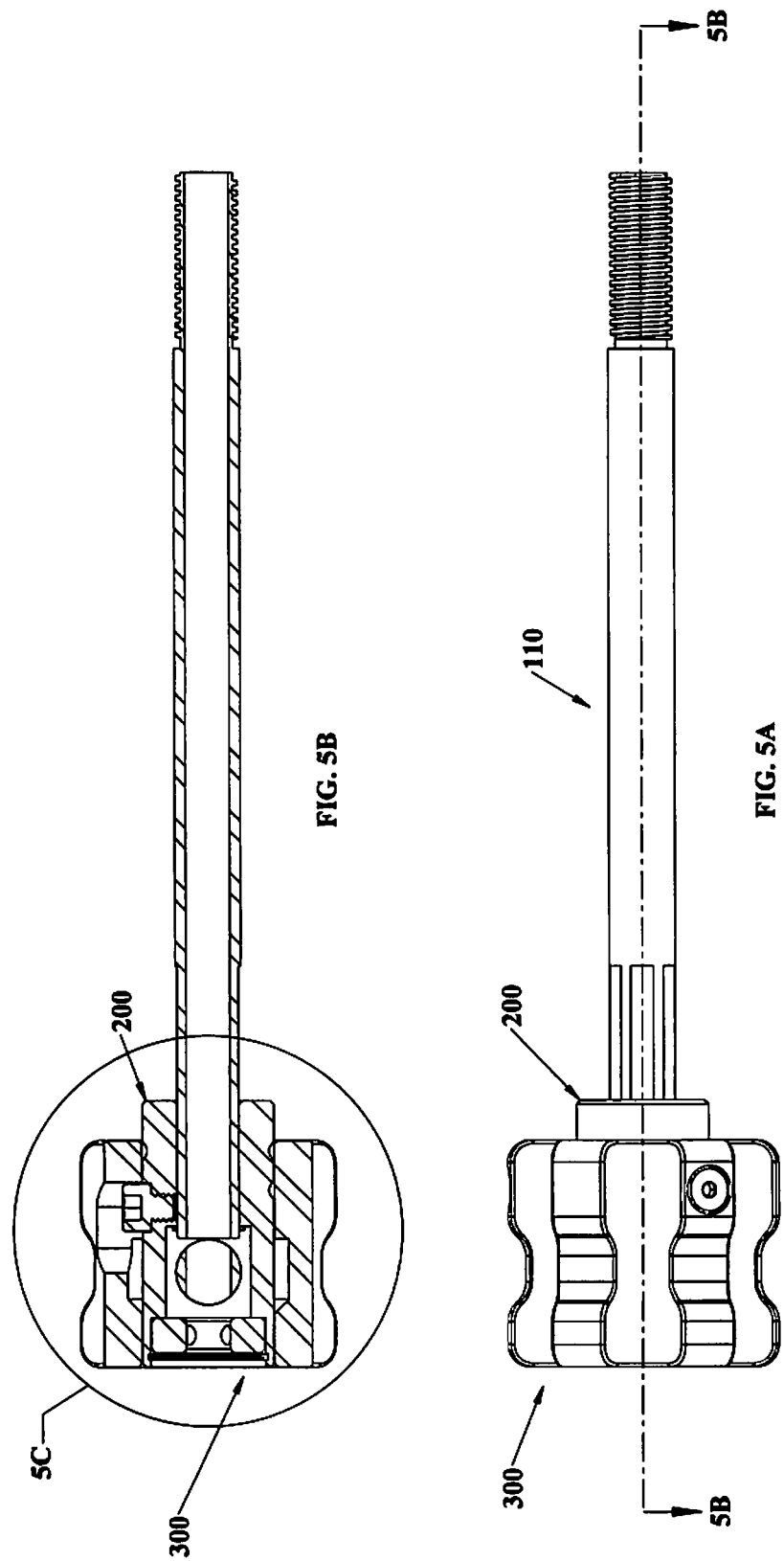

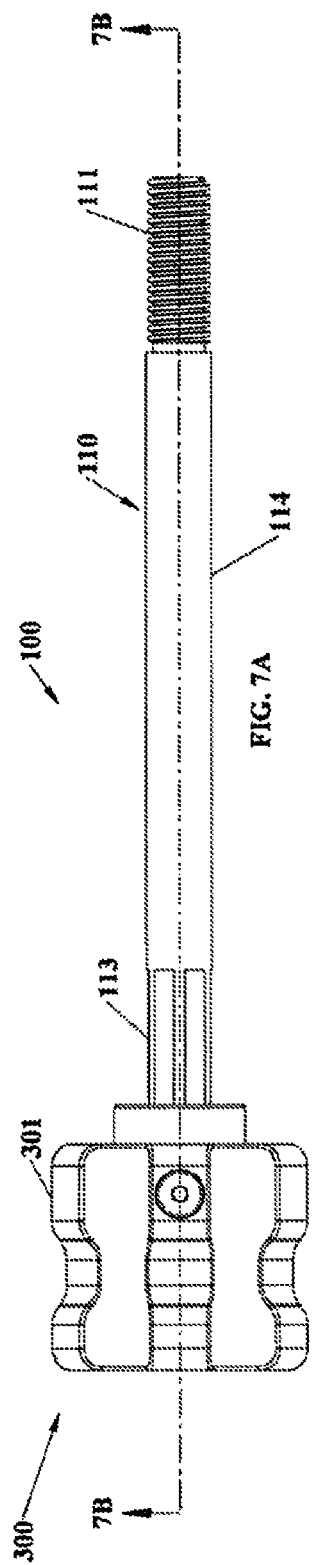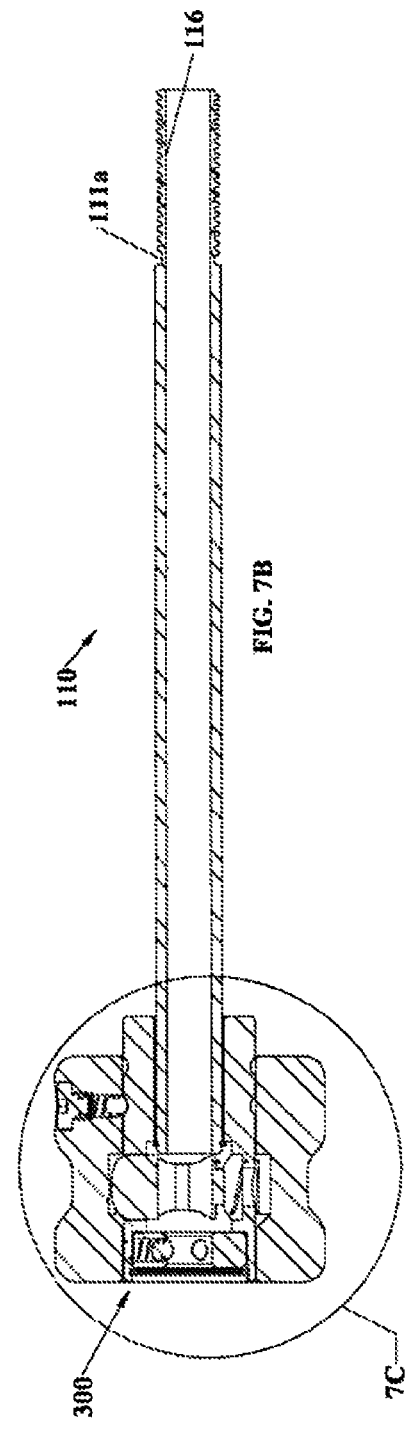

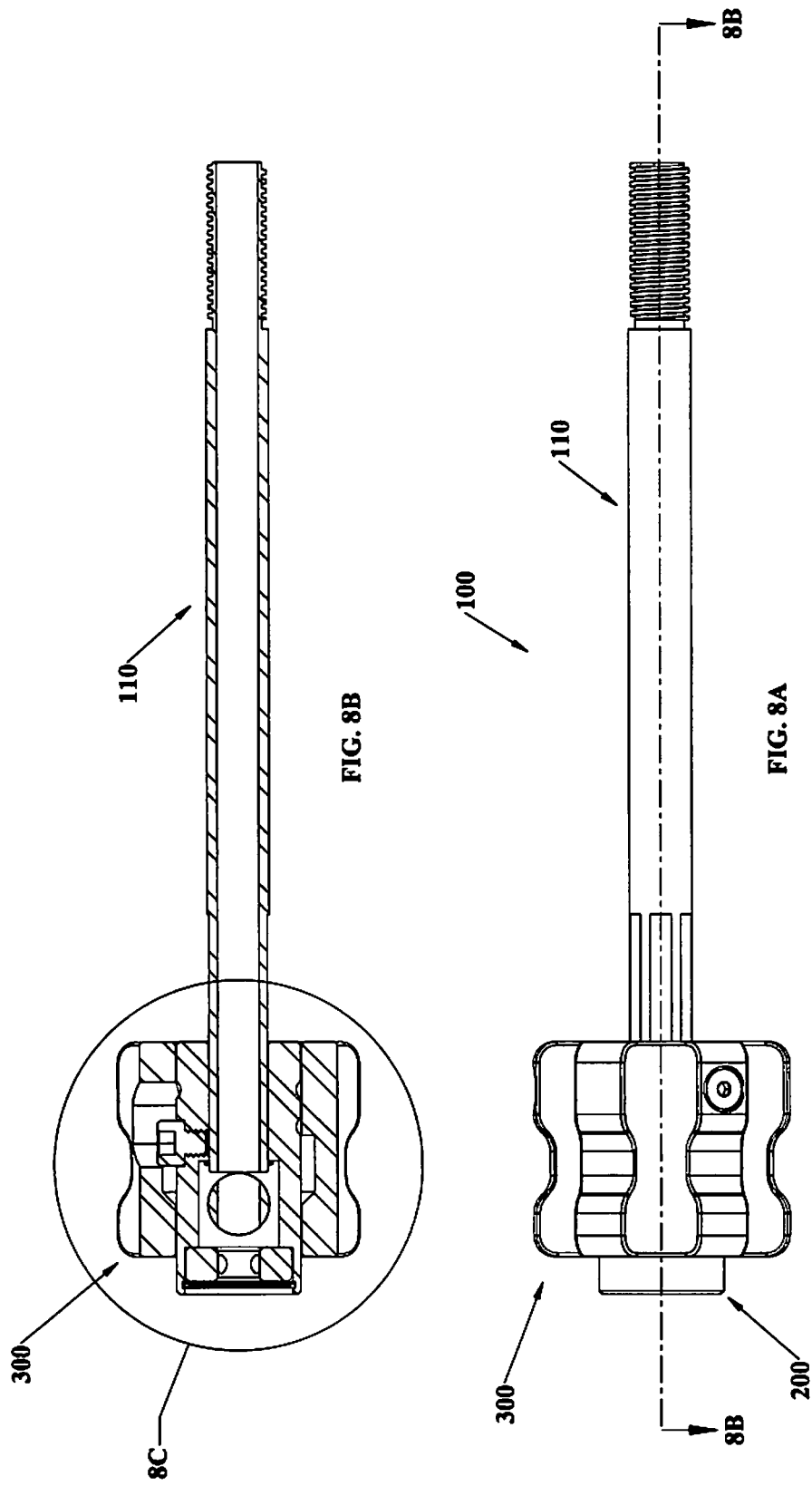

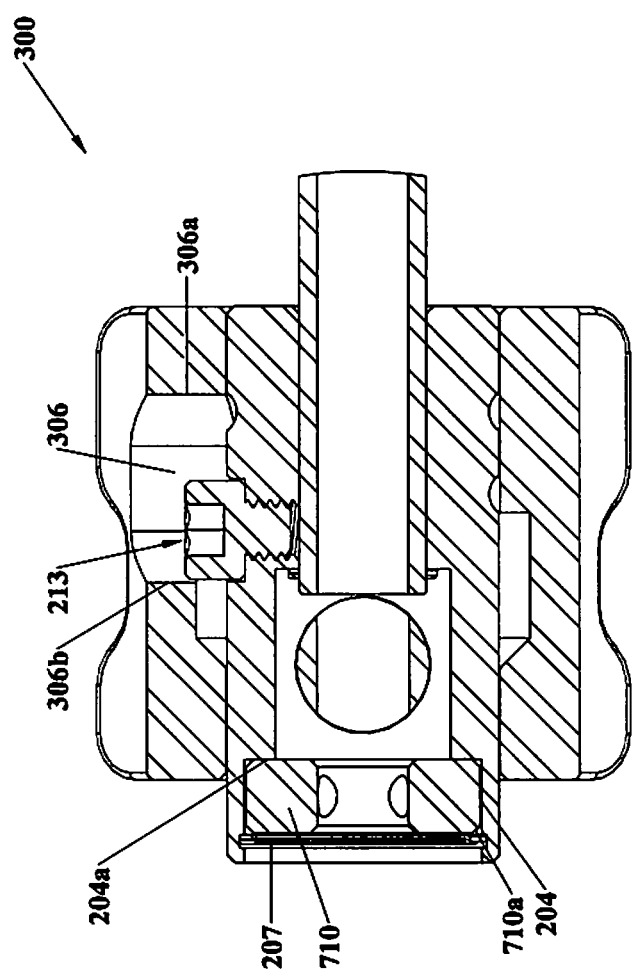

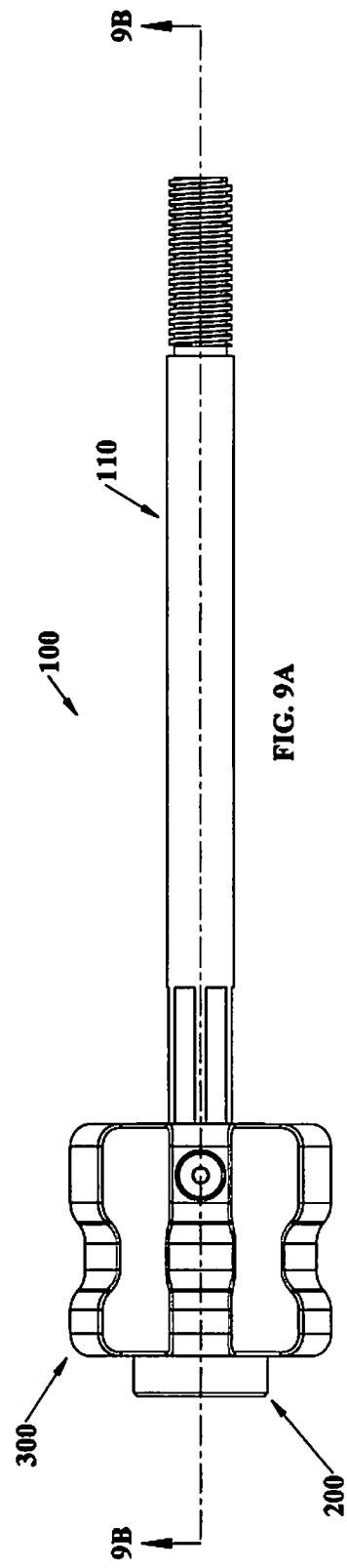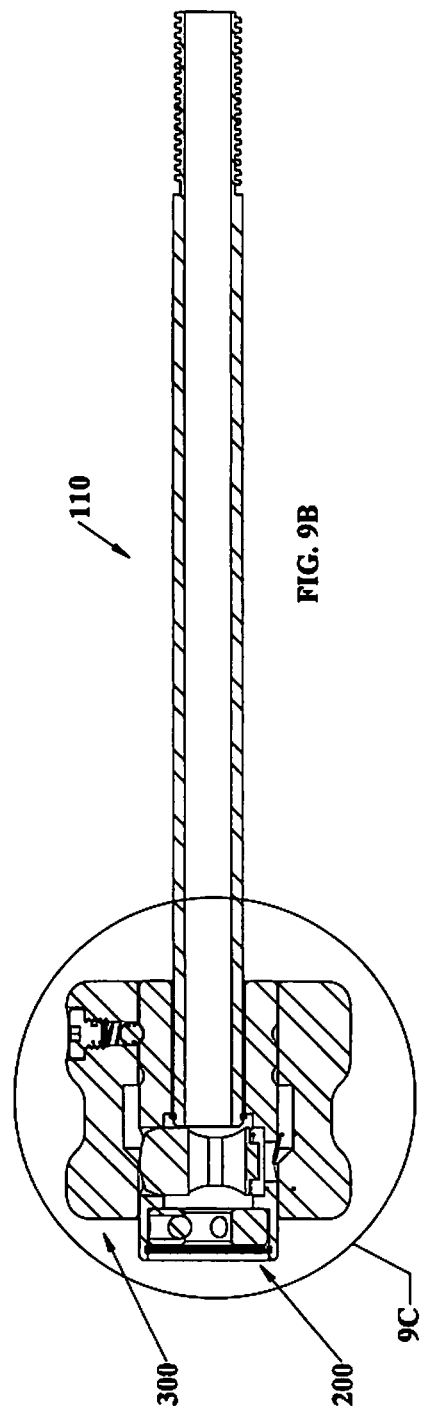
FIG. 9A
FIG. 9B

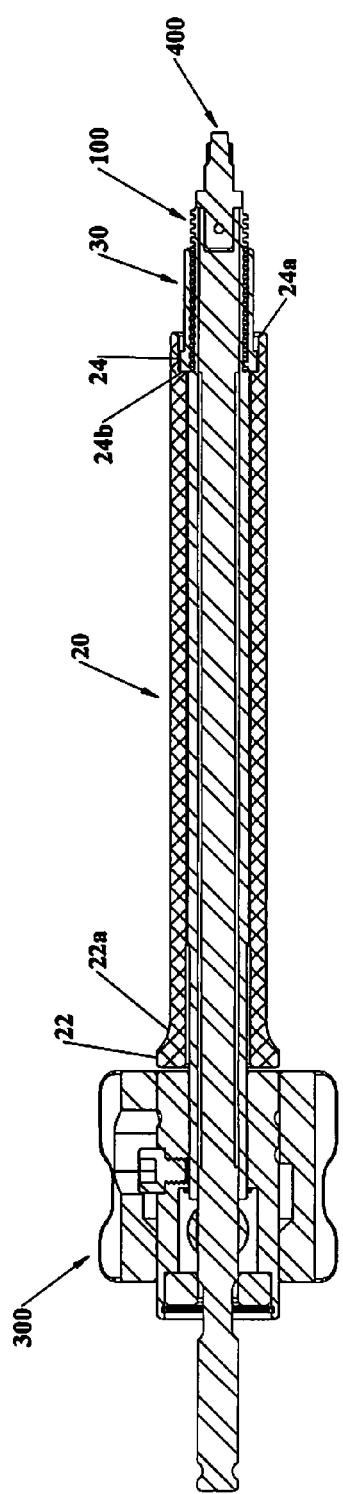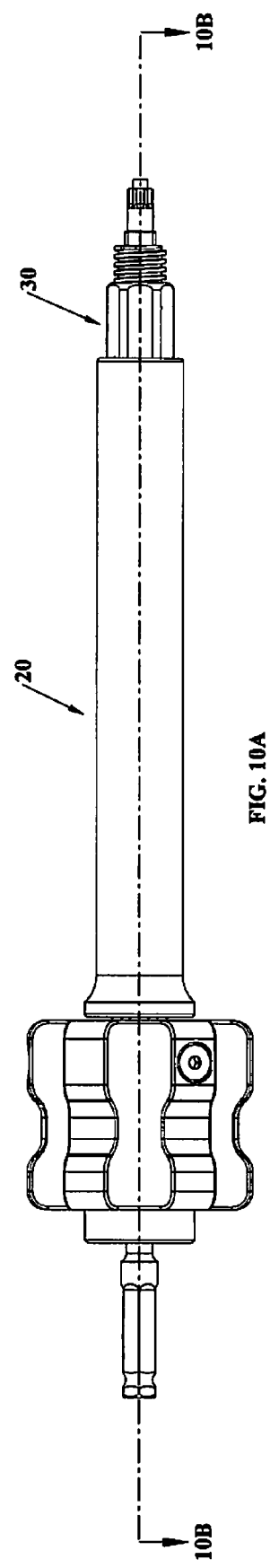
FIG. 10B
FIG. 10A

SCREW INSERTION INSTRUMENT

BACKGROUND

Technical Field

The present disclosure relates generally to instruments and methods for orthopedic spine surgery and, in particular, to a screw insertion instrument for selectively coupling to a pedicle screw and a method of operating the same.

Background of the Disclosure

Spinal fixation apparatus are widely employed in surgical processes for correcting spinal injuries and diseases. In order to facilitate stabilizing the spine and maintaining vertebral bodies in a desired alignment, implants such as longitudinally linked rods are secured to coupling elements, which in turn are secured to vertebral bodies by fasteners such as pedicle screws.

Many pedicle screws utilize a coupling element in the form of a tulip, which engages the pedicle screw head and is pivotable and rotatable in relation to the axis of the screw shank (i.e. polyaxial to the shank axis). While this ability more easily facilitates alignment of the tulip with the longitudinally linked rods, it may cause the screw to be difficult to handle. A means for ensuring the pedicle screw remains secured to an insertion instrument provides more positive control over the placement of the pedicle screw. Furthermore, this permits control over the trajectory of the pedicle screw so that it may be more accurately secured to the vertebral body (i.e. the pedicle screw must be rigid such that the shank of the pedicle screw is fixed in relation to the insertion instrument). Therefore, many polyaxial pedicle screw drivers are designed to engage the pedicle screw such that the tulip and shank of the screw are rigidly coupled, thereby permitting the pedicle screw to be driven into the vertebra with greater control.

One example of an instrument is disclosed in U.S. Pat. No. 8,231,635. The disclosed insertion instrument includes a polyaxial screwdriver wherein the polyaxial screwdriver both threads into the tulip of the pedicle screw and engages the head of the pedicle screw to maintain the tulip and screw in a rigid configuration relative to each other. The polyaxial screwdriver further includes a locking mechanism to couple the polyaxial screwdriver to the pedicle screw such that the pedicle screw cannot rotate with respect to the polyaxial screwdriver. The locking mechanism further prevents the polyaxial screwdriver accidentally unthreading from the tulip of the pedicle screw (i.e. a one way ratcheting system is employed). In order to remove the polyaxial screwdriver from the pedicle screw, a button must be pressed and held which releases the ratchet and permits the polyaxial screwdriver to be unthreaded from the tulip without backing out the pedicle screw from the vertebral body.

It would be preferable, however, if the clinician can selectively lock or unlock the driving member of the screw insertion instrument such that the instrument remains in the position in which the clinician left it (i.e. the clinician does not need to continuously provide input to keep the pedicle screwdriver disengaged from the screw head).

There remains a need for an instrument for inserting spinal anchors.

SUMMARY

The present disclosure is directed to an instrument for selectively coupling with a pedicle screw including an inner shaft and a knob assembly. The inner shaft is an elongate body having a distal tip configured to engage the head of a pedicle screw. The knob assembly includes a tubular body, wherein the inner shaft is disposed within the tubular body such that the inner shaft is free to rotate but not translate axially with respect to the tubular body. A distal end of the tubular body is also configured to engage a tulip of the pedicle screw. The knob assembly further includes a knob that is supported by the tubular body such that the knob is free to translate axially along the tubular body, but not rotate relative to it. The knob is also selectively engageable with the inner shaft.

The instrument may also include a sleeve adapted to receive the tubular body such that the sleeve is disposed between the knob and the distal end of the tubular body. The instrument may also include a nut configured to be in mechanical cooperation with the distal end of the tubular body.

In one aspect, the inner shaft may include a set of splines on a proximal end or region extending distally along a longitudinal axis as defined by the elongate body of the inner shaft.

The knob may also include a set of splines on a proximal end or region of the knob to be selectively engageable with the splines of the inner shaft.

The knob may also include a hexagonal cross section extending through a longitudinal bore defined between the proximal and distal ends of the knob.

The tubular body may also include a hexagonal cross section extending distally along a longitudinal axis defined by the proximal and distal ends of the tubular body to be engaged by the hexagonal cross section of the knob.

Another embodiment of the instrument may include a detent assembly for selectively locking the knob in a first or second position along the longitudinal axis.

The instrument may also include a through hole, having proximal and distal ends, wherein the through hole extends radially inward from the outer surface of the knob towards the second longitudinal bore, wherein the through hole is configured to receive the detent assembly such that the detent assembly is prevented from passing entirely through the distal end of the through hole. Further, the instrument may also include two grooves configured to engage the detent assembly. The two grooves are longitudinally spaced such that the knob may be selectively locked in one of the two grooves by the detent assembly. The detent assembly has a detent ball configured to be received by the through hole but not advance entirely therethrough, a detent set screw, including a head and a threaded shank extending distally therefrom, the detent set screw configured to engage the through hole, and a detent spring, having proximal and distal ends. The detent spring is disposed within the through hole such that the detent spring is located between the detent ball and detent set screw thereby biasing the detent ball radially inward.

A further embodiment of the instrument may include a crenellated outer surface.

According to yet another aspect, the present disclosure is directed to a method for coupling an insertion instrument to a pedicle screw. The method includes providing an insertion instrument having an inner shaft having a tip configured to engage a pedicle screw and a knob assembly configured to engage a tulip of the pedicle screw. The proximal end of the knob assembly supports a knob, wherein the knob is selectively engageable with the inner shaft. The method involves inserting the tip of the inner shaft into a head of the pedicle screw, threading the knob assembly into the tulip of the pedicle screw, and advancing the knob distally such that the knob is in mechanical cooperation with the inner shaft.

The method may also include advancing a handle sleeve over the knob assembly. The method may further include securing a nut to the knob assembly such that the handle sleeve is rotatably and translatably supported by the knob assembly. The method may further include advancing the knob assembly over the inner shaft.

A further aspect of the method may also include the instrument having a first set of splines along a longitudinal axis defined by the proximal and distal ends of the inner shaft, and a second set of splines disposed within a longitudinal bore of the knob, wherein distal advancement of the knob results in engagement between the first and second sets of splines.

Yet another aspect of the method may include the instrument having a hexagonal cross section on the distal end of the longitudinal bore of the knob, and an outer surface of the tubular body may include a hexagonal cross section to be engaged by the hexagonal cross section of the knob, wherein rotation of the knob causes rotation of the tubular body causing the knob assembly to thread into the tulip of the pedicle screw.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4 is a perspective view of the knob assembly of FIG. 2;

FIG. 5A is a side view of the knob assembly of FIG. 4;

FIG. 5B is cross-sectional view of the knob assembly of FIG. 5A taken along section line 5B-5B;

FIG. 7A is a side view of the knob assembly showing the detent screw;

FIG. 7B is a cross-sectional view of the knob assembly of FIG. 7A taken along section line 7B-7B;

FIG. 8A is a side view of the knob assembly in a locked position;

FIG. 8B is a cross-sectional view of the knob assembly of FIG. 8A taken along section line 8B-8B;

FIG. 8C is an enlarged view of the area of detail of FIG. 8B;

FIG. 9A is a side view of the knob assembly in a locked position show in the detent screw;

FIG. 9B is a cross-sectional view of the knob assembly of FIG. 9A taken along section line 9B-9B;

FIG. 10A is a side view of the screw insertion instrument of FIG. 1;

FIG. 10B is a cross-sectional view of the screw insertion instrument of FIG. 10A taken along section line 10B-10B;

DETAILED DESCRIPTION OF THE EMBODIMENTS

Figure 1:
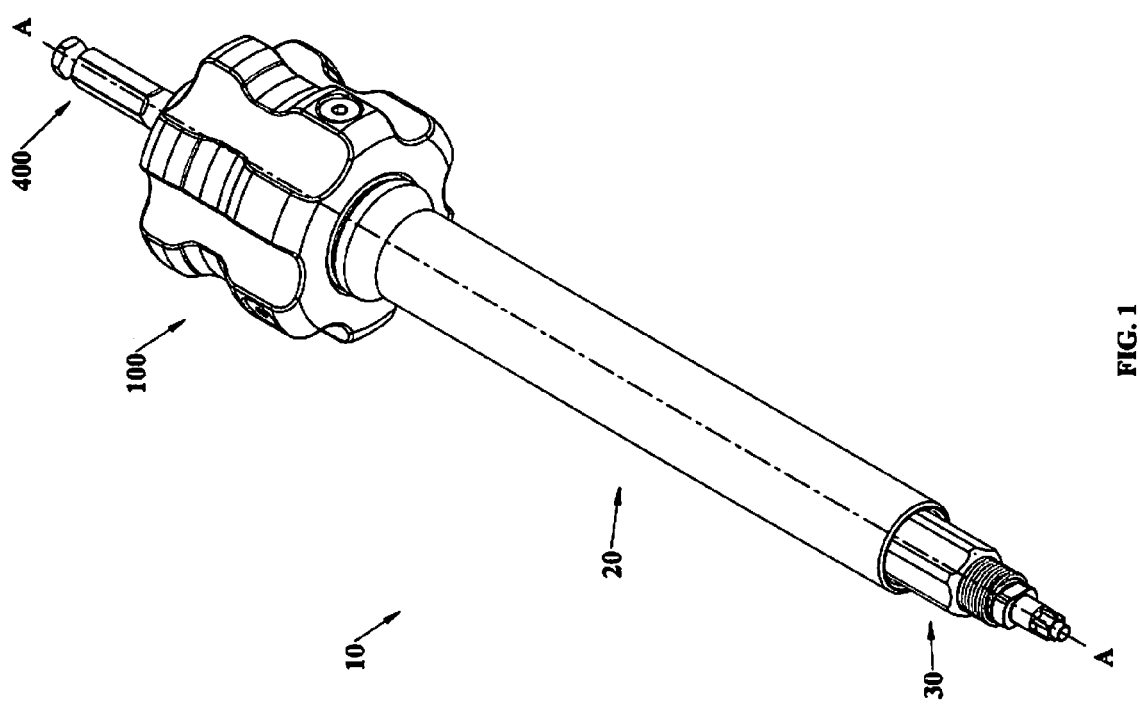
FIG. 1 is a perspective view showing the a screw insertion instrument for selectively coupling with a pedicle screw.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 2:
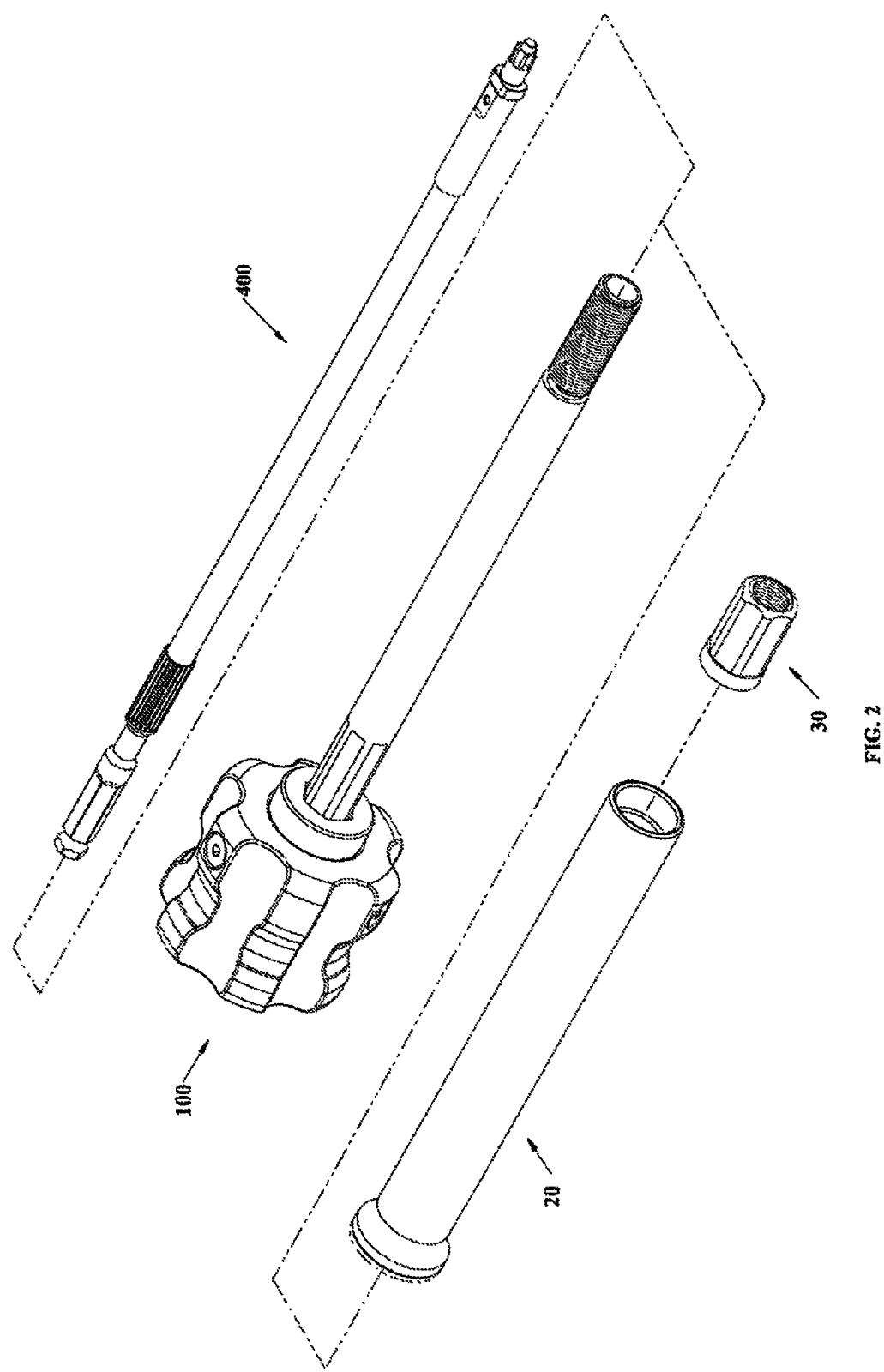
FIG. 2 is an exploded view, with parts separated, of the locking screw insertion instrument of FIG. 1.

Referring now to the drawings, FIGS. 1 and 2 illustrate an embodiment of screw insertion instrument 10 for selectively coupling to a pedicle screw 800 (FIGS. 13 and 13A-C). The embodiment of screw insertion instrument 10 shown in FIGS. 1 and 2 includes a handle sleeve 20, a handle sleeve nut 30, a knob assembly 100, and an inner shaft 400 which are coaxially aligned with axis A-A. Knob assembly 100 provides rotational and translational support for inner shaft 400 and handle sleeve 20. Inner shaft 400 is disposed within support shaft 110 of knob assembly 100 whereas handle sleeve 20 is advanced over knob assembly 100. The distal end of knob assembly 100 provides a mounting point for handle sleeve nut 30. Handle sleeve 20 and handle sleeve nut 30 combine to provide translational support for knob assembly 100, such that knob assembly 100 may advance proximally, but not distally along axis A-A as the knob assembly 100 would abut handle sleeve 20. Portions of handle sleeve 20, handle sleeve nut 30, knob assembly 100 and inner shaft 400 may be made of any suitable biocompatible material, including but not limited to, titanium, titanium alloys, stainless steel, cobalt chrome, nickel titanium or polymer compositions.

Figure 3:
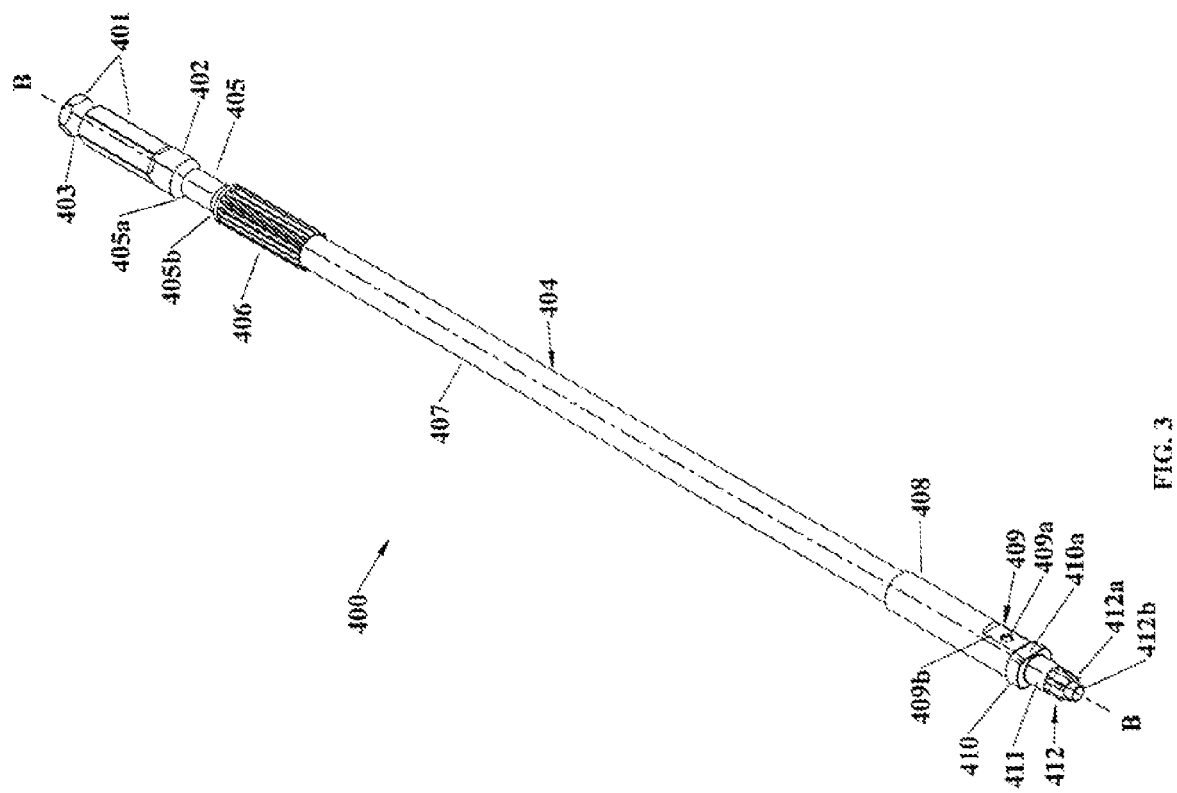
FIG. 3 is a perspective view of the inner shaft of FIG. 2.
Figure 5C:
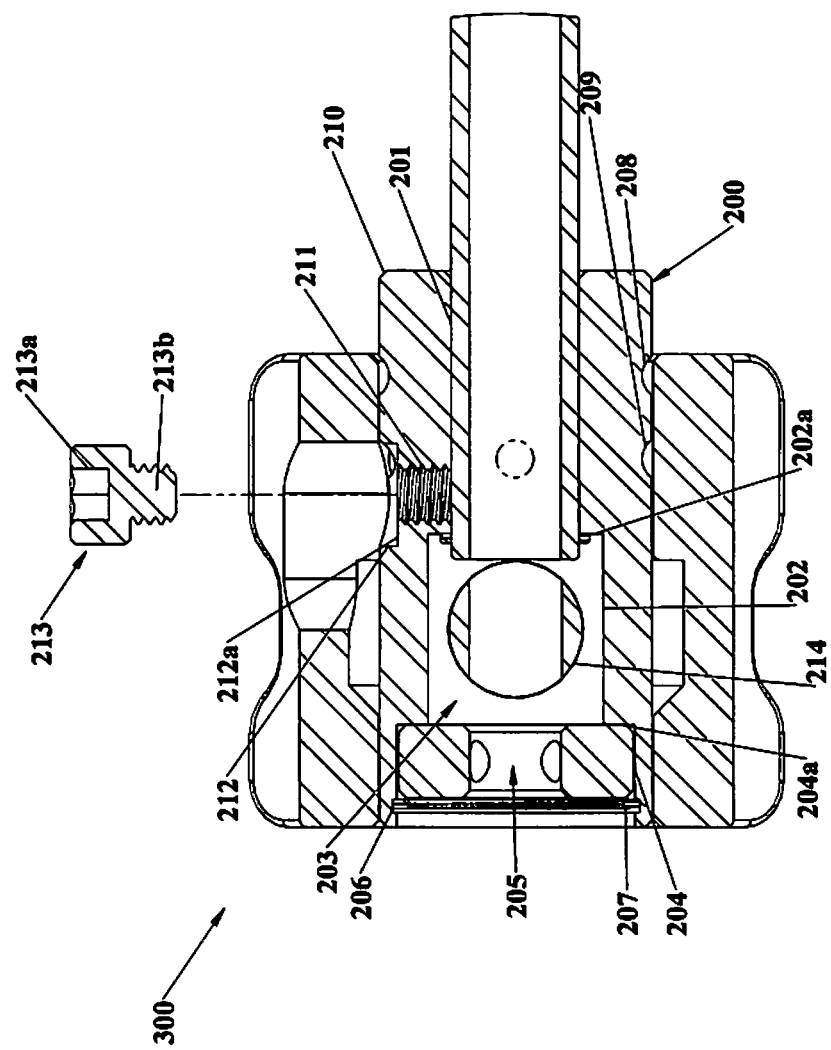
FIG. 5C is an enlarged view of the area of detail of FIG. 5B.

Inner shaft 400, as shown in FIG. 3, includes an elongate body 404 including a proximal end and a distal tip defining longitudinal axis B-B. The proximal end of elongate body 404 includes a hexagonal cross section 401 transitioning to a circular cross section 402 extending distally along axis B-B. A groove 403 is disposed between the proximal end of elongate body 404 and circular cross section 402 and extends radially inward. Groove 403 may have a circular cross section and may extend circumferentially around axis B-B. Circumferential groove 403 is oriented normal to axis B-B such that axis B-B extends through the centerpoint of circumferential groove 403. Circular cross section 401 transitions to a first shank portion 405 having a diameter less than that of circular cross section 401. The proximal end of first shank portion 405 include an edge which includes a radius 405a to transition from the larger diameter of circular cross section 401 to the smaller diameter of first shank portion 405. The distal end of first shank portion 405 includes radius 405b to transition back to a diameter generally the same as circular cross section 401.

Extending distally along axis B-B from distal radius 405b are longitudinal splines 406. Longitudinal splines 406 are arranged radially with a major diameter corresponding to the outer diameter of radius 405b and have a minor diameter corresponding to second shank portion 407, having a circular cross section, extending distally therefrom. The distal end of second shank portion 407 transitions to a third shank portion 408 having a circular cross section. The distal end of third shank portion 408 includes recess 409 cut into the circular cross section such as to form a planar surface 409b having reduced width as compared to the diameter. Recess 409 may include two planar surface 409b on opposing sides of axis A-A. Recess 409 includes a through hole 409a bored entirely though third shank portion 408. Through hole 409a may be normal to flat surface 409b. Immediately adjacent to recess 409 is a flange 410 having an outer diameter greater than that of third shank portion 408, but with flat surfaces 410b having identical width to that of planar surface 409b of recess 409. Flange 410 acts as a stop when inner shaft 400 is advanced through knob assembly 100 such that flange 410 abuts the distal end of knob assembly 100 when advanced therethrough.

Extending distally from flange 410 is fourth shank portion 411 having a diameter less than or equal to the width of planar surface 409b. Extending distally from fourth shank portion 411 is a distal tip 412. Distal tip 412 is configured to engage a head 810 of a pedicle screw 800 such that the pedicle screw 800 is in mechanical cooperation with inner shaft 400 (see FIGS. 13 and 13C). Any means known in the art to transmit the rotational motion of inner shaft 400 to the head 810 of the pedicle screw 800 may be employed. Such means may be square, hex, pozidrive, or the like. In one non-limiting embodiment of inner shaft 400, distal tip 412 includes a hexalobe pattern 412a. Distal tip 412 may also include a cylindrical projection 412b extending distally from hexalobe pattern 412a. Cylindrical projection 412b serves to align inner shaft 400 coaxially with the pedicle screw along axis B-B.

Referring now to FIG. 4, an embodiment of knob assembly 100 is shown. Knob assembly 100 includes a support shaft 110, a knob sleeve 200 and a knob 300 which are coaxially aligned with axis C-C.

Figure 7C:
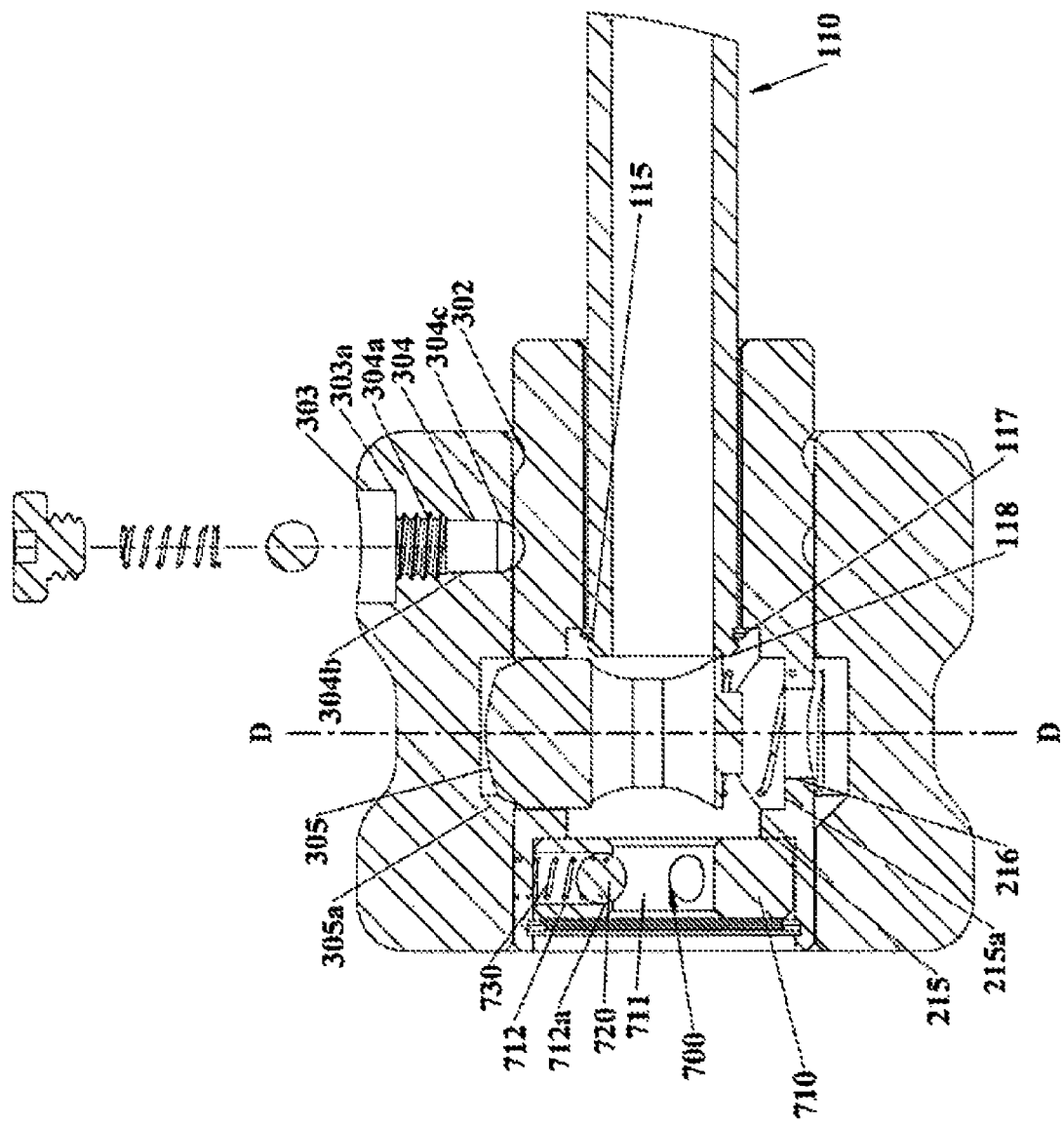
FIG. 7C is an enlarged view of the area of detail of FIG. 7B.

Support shaft, or tubular body, 110 as illustrated in FIGS. 7A-C, includes a proximal end and a distal end. A longitudinal bore 116 is defined between the proximal and distal ends of support shaft 110. The diameter of longitudinal bore 116 is such that inner shaft 400 can be advanced therethrough and flange 410 of inner shaft 400 abuts the distal end of support shaft 110. The distal end of support shaft 110 includes a threaded tip 111 having proximal and distal ends configured to engage a tulip 820 of a pedicle screw 800 (see FIGS. 13 and 13C). The proximal end of threaded tip 111 includes an undercut 111a. Extending proximally from undercut 111a is an unthreaded portion 114. Unthreaded portion 114 has an outer diameter greater than or equal to the major diameter of threaded tip 111 such that handle sleeve 20 may be advanced thereover. Undercut 111a includes a diameter equal to the minor diameter of threaded tip 111. Unthreaded portion 114 transitions into a section 113 having a hexagonal configuration. Section 113 includes flat widths less than the outer diameter of unthreaded portion 114. The proximal end of section 113 includes a retaining ring groove 115. Retaining ring groove 115 is configured to accept a first retaining ring 117. First retaining ring 117 may be any retaining ring known in the art such as spiral retaining rings, a circlip, snap rings, or the like. One non-limiting embodiment of first retaining ring 117 is of the spiral retaining ring type. First retaining ring 117 serves to prevent knob sleeve 200 from advancing proximally along axis C-C with respect to support shaft 110. First retaining ring 117 may be constructed of any biocompatible material, including but not limited to, titanium, titanium alloys, stainless steel, cobalt chrome, and nickel titanium or polymer compositions. In one non-limiting embodiment of support shaft 110, the proximal end of 113 may include a chamfer 118.

FIGS. 4, 5A-C, and 7A-C illustrate knob sleeve 200. Knob sleeve 200 is circular in cross section and has open proximal and distal ends which define a lumen 201 therethrough. Lumen 201 is hexagonal in cross section and is configured to be in mechanical cooperation with section 113 of support shaft 110 such that knob sleeve 200 may advance or retract along axis C-C, but not rotate with respect to support shaft 110. A first counterbore 202 having a circular cross section extends distally along axis C-C defining a first cavity 203 therein. First counterbore 202 terminates with a first face 202a wherein retaining ring 117 may abut thereby prohibiting knob sleeve 200 from advancing proximally past retaining ring 117 along axis C-C with respect to support shaft 110.

First counterbore 202 includes a first through hole 214 having open proximal and distal ends defining axis D-D (see FIG. 7C), wherein axis D-D is normal to axis C-C. First through hole 214 extends from the outer surface of knob sleeve 200 and into first cavity 203. Coaxial with first through hole 214 is a counterbore 215 extending radially outward from an inner surface of first cavity 203 directly opposite from first through hole 214. Counterbore 215 includes a diameter equal to that of first through hole 214 and terminates in a surface 215a. One non-limiting embodiment of knob sleeve 200 includes a second through hole 216 having open proximal and distal ends. Second through hole 216 extends radially outward from surface 215a and penetrates the outer surface of knob sleeve 200. Second through hole 216 is coaxial with axis D-D and includes a diameter less than that of counterbore 215.

A third counterbore 204 having a circular cross section and proximal and distal ends, extends distally along axis C-C defining a second cavity 205 therein. Third counterbore 204 terminates with a second face 204a. The proximal end of third counterbore 204 includes an internal groove 206 extending radially outward from the surface of cavity 205. Groove 206 is configured to receive a second retaining ring 207. Second retaining ring 207 may be any retaining ring known in the art such as spiral retaining rings, a circlip, snap rings, or the like. One non-limiting embodiment of second retaining ring 207 is of the spiral retaining ring type. Second retaining ring 207 may be constructed of any biocompatible material, including but not limited to, titanium, titanium alloys, stainless steel, cobalt chrome, and nickel titanium or polymer compositions.

The distal end of an outer surface of knob sleeve 200 includes a first groove 208. First groove 208 is of circular cross section and extends radially inward enabling knob 300 to lock in a distal position. First groove 208 may extend circumferentially around axis C-C such that axis C-C extends through the center point of groove 208. At a position proximal to first groove 208, a second groove 209 of circular cross section extends radially inward enabling knob 300 to lock in a proximal, or first, position. Second groove 209 may be oriented in the same manner as first groove 208.

Disposed between second groove 209 and first flat face 202a is a through hole 211 having internal threads and having an open entrance and exit, extending radially outward in a direction normal to axis C-C. A counterbore 212 extends radially inward from the entrance of through hole 211 and is configured to accept a set screw 213. Counterbore 212 terminates with a face 212a such that set screw 213 can be secured thereto. Set screw 213, having proximal and distal ends, includes a head 213a on the proximal end and a threaded shank 213b extending distally therefrom configured to be threaded into through hole 211. The length of threaded shank 213b is such that set screw 213 does not come into contact with section 113 of support shaft 110 when fully tightened against face 212a. Head 213a, when set screw 213 is fully tightened against face 212a, extends radially outward a distance greater than the outer diameter of knob sleeve 200. Set screw 213 acts as a motion limiter of knob 300 such that knob 300 is limited to advancing distally to a position where knob 300 is locked within first groove 208, and limited to advancing proximally to a position where knob 300 is locked within second groove 209. A non-limiting embodiment of knob sleeve 200 may include chamfer 210 on the proximal and distal edges of the outer surface of knob sleeve 200, the distal edge of lumen 201 and the proximal edge of third counterbore 204.

Referring now to FIGS. 7A-7C, an embodiment of knob 300 is illustrated. Knob 300 includes a crenellated outer surface 301 having open proximal and distal ends defining a lumen 302 therein. Crenellated outer surface 301 is of the overall shape depicted in FIGS. 7A-7C. This overall shape enables the clinician to easily handle and grip the knob. The distal end of crenellated outer surface 301 includes a counterbore 303 extending radially inward towards lumen 302. Counterbore 303 terminates in a surface 303a. Extending radially inward from surface 303a is a through hole 304 having open proximal and distal ends. Through hole 304 includes a threaded proximal end 304a, a tapered distal end 304c and a smooth bore 304b disposed therebetween. Smooth bore 304b includes a diameter equal to the minor diameter of threaded proximal end 304a. Tapered distal end 304c tapers in a spherical fashion as to accept a spheroid such that the spheroid may not pass entirely therethrough.

Disposed within through hole 304 is detent assembly 500. Detent assembly 500 includes detent set screw 501, detent spring 502 and detent ball 503 (see FIGS. 9A-9C).

Detent set screw 501 includes a head 501a and a threaded shank 501b extending distally therefrom. Head 501a is configured to be accepted by counterbore 303 and threaded shank 501b is configured to thread into threaded proximal end 304a. The length of threaded shank 501b is such that set screw 501 may be fully tightened against surface 303a without having threaded shank 501b contact smooth bore 304b. A non-limiting embodiment of head 501a may be low profile such that it does not extend radially outward past crenellated outer surface 301.

Detent ball 503 is a spheroid and includes a diameter less than smooth bore 304b but large enough to be engaged by tapered distal end 304c as to not pass entirely therethrough.

Disposed between detent set screw 501 and detent ball 503 is detent spring 502. Detent spring 502 is axially supported by smooth bore 304b and is compressed between detent set screw 501 and detent ball 503 such that detent ball 503 is biased towards lumen 302. The bias of detent ball 503 towards lumen 302 generates a detent action that enables detent ball 503 to engage first groove 208 when knob 300 is in a distal, or second, position, and engage second groove 209 when knob 300 is in a proximal position. This detent action serves to lock knob 300 in each position, requiring an external force by the clinician along axis C-C to advance knob 300 in either direction.

Knob 300 may include a plurality of counterbore 303 and detent assembly 500. One non-limiting embodiment of knob 300 includes three (3) each of counterbore 303 and detent assembly 500.

Lumen 302 includes a groove 305 extending radially outward therefrom. Groove 305 includes a width extending between proximal and distal ends equal to that of the diameter of first through hole 214. The proximal end of groove 305 includes a chamfer 305a and the distal end includes a face 305b. Chamfer 305a extends proximally from groove 305 and may be of any obtuse angle with respect to the inner surface of groove 305. Groove 305 is located such that when knob 300 is in a proximal position and locked within second groove 209, axis D-D, as defined by first through hole 214, bisects groove 305.

Figure 6:
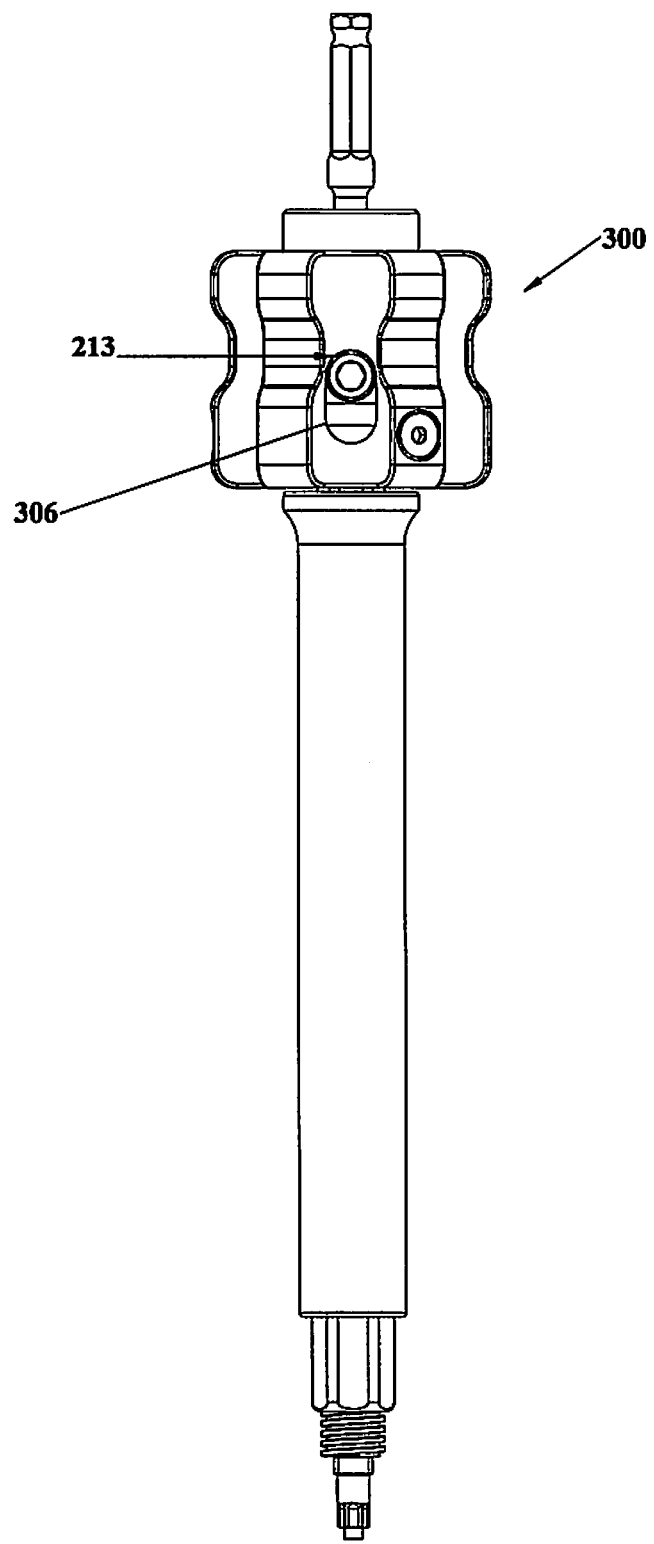
FIG. 6 is a side view of the knob assembly showing a motion limiting set screw.

Referring now to FIGS. 6 and 8C, knob 300 further includes a slot 306. Slot 306 extends through crenellated outer surface 301 and through an inner surface of lumen 302. Slot 306 includes a width such that set screw 213 can be disposed therein. The length of slot 306 extends in a direction parallel to axis C-C, and is such that set screw head 213a abuts a proximal end of slot 306 when knob 300 is in a distal position, and set screw head 213a abuts a distal end of slot 306 when knob 300 is in a proximal position. When operated in conjunction, slot 306 and set screw head 213a serve to limit the longitudinal motion of knob 300 such that knob 300 and detent assembly 304 will lock within first groove 208 and second groove 209 in a distal and proximal position respectively.

Figure 9C:
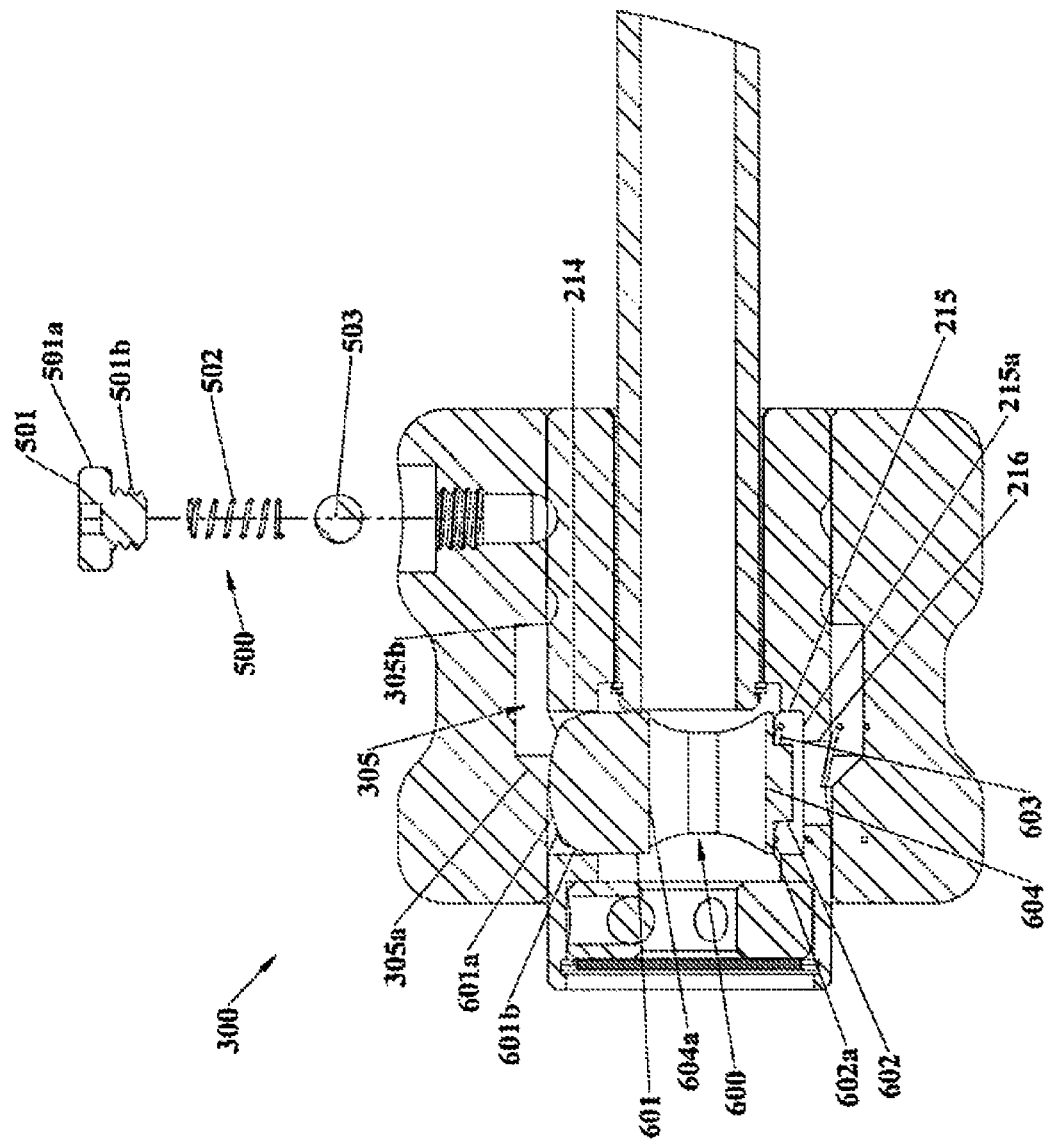
FIG. 9C is an enlarged view of the area of detail of FIG. 9B.

FIG. 9C illustrates an engagement button assembly 600. Engagement button assembly 600 includes an engagement button 601 and an engagement button spring 603.

Engagement button 601 is cylindrical in cross section and includes proximal and distal ends. The outer diameter of engagement button 601 is such that it engages first through hole 214 by a slip fit. The proximal end of engagement button 601 includes a spherical dome 601a. One non-limiting embodiment of spherical dome 601a is of generally large radius; however, spherical dome 601a can be of any radius greater than or equal to the outer diameter of button 600. The proximal end of engagement button 600 further includes a chamfer 601b. Chamfer 601b runs circumferentially about the proximal end of engagement button 600 such that the transition from the outer diameter of engagement button 600 to spherical dome 601a is more gradual. Chamfer 601b may include any angle with respect to the outer surface of engagement button 600 between zero (0) and ninety (90) degrees such that chamfer 601b extends radially inward from the outer surface of engagement button 600. The distal end of engagement button 600 further includes boss 602. Boss 602, having proximal and distal ends, extends distally from the distal end of engagement button 600 and includes an outer diameter less than that of the outer diameter of engagement button 600, and such that the distal end of boss 602 may pass through second through hole 216. The proximal end of boss 602 extends from a face 602a, which includes the annular space between the outer diameter of engagement button 600 and the outer diameter of boss 602. Engagement button 600 further includes a bore 604 having open proximal and distal ends. Bore 604 extends normal to the outer surface of engagement button 600 and includes a smooth inner bore for approximately ¾ of its circumference on the surface closest to the distal end of engagement button 600. The remaining approximately ¼ circumference of the inner bore closest to the proximal end of engagement button 600 includes splines 604a configured such that they may engage splines 406 of inner shaft 400 when inner shaft 400 is disposed therein. Spines 604a extend from the open proximal end to the open distal end of engagement button 600 along axis C-C.

Engagement button spring 603, having proximal and distal ends, is disposed between face 602a of engagement button 600 and surface 215a of counterbore 215 when engagement button 600 is disposed within first through hole 214. The proximal end of engagement button spring 603 abuts face 602a and the distal end of engagement button spring 603 abuts surface 215a and biases engagement button 600 such that when knob 300 is in a proximal position engagement button 600 rests within groove 305 and is coaxially aligned with axis D-D (see FIG. 7C). In this position, splines 604a are not engaged with splines 406 thus permitting knob assembly 100 to rotate with respect to inner shaft 400 about axis A-A (See FIG. 1). Referring now to FIG. 9C, an illustration of knob 300 in a distal position is provided. As knob 300 is advanced to a distal position, chamfer 305a of groove 305 acts against chamfer 601b of engagement button 600 such that engagement button 600 is driven distally along axis D-D. In this distal position of knob 300, splines 604a are engaged with splines 406 causing knob assembly 100 to be in mechanical engagement (i.e. coupled) with inner shaft 400 permitting the clinician to drive a pedicle screw 800 into a vertebral body VB.

As illustrated in FIGS. 7A-8C, an inner shaft detent assembly 700 is disposed within second cavity 205 defined by third counterbore 204 of knob sleeve 200. Inner shaft detent assembly 700 includes an inner shaft detent cage 710, an inner shaft detent ball 720, and an inner shaft detent spring 730.

Inner shaft detent cage 710, having proximal and distal ends, is circular in cross section and includes a longitudinal bore 711 having open proximal and distal ends. The outer surface of inner shaft detent cage 710 includes a diameter such that inner shaft detent cage 710 may be disposed within third counterbore 204 by means of slip fit. The overall length of inner shaft detent cage 710 is such that the proximal end abuts second retaining ring 207 and the distal end abuts second face 204a thereby prohibiting inner shaft detent cage 710 from advancing proximally or distally along axis C-C. Extending radially inward from the outer surface of inner shaft detent cage 710 is a radial bore 712. A plurality of radial bore 712 may exist such that each radial bore 712 is equally spaced circumferentially around the outer surface of inner shaft detent cage 710. Radial bore 712 includes open proximal and distal ends with a smooth bore including a diameter larger than inner shaft detent ball 720 and inner shaft detent spring 730. The distal end of radial bore 712 is tapered in a spherical fashion as to accept inner shaft detent ball 720 such that inner shaft detent ball 720 may not pass entirely therethrough.

Disposed within radial bore 712 is inner shaft detent ball 720. Inner shaft detent ball 720 is a spheroid with a diameter less than that of radial bore 712, but large enough to be engaged by the tapered distal end of radial bore 712 as to not pass entirely therethrough.

Radial bore 712 further includes inner shaft detent spring 730 disposed therein. Inner shaft detent spring 730 includes proximal and distal ends. Inner shaft detent spring 730 is axially supported by radial bore 712 and is compressed between inner shaft detent ball 720 and the inner surface of third counterbore 204. The compression of inner shaft detent spring 730 biases inner shaft detent ball 720 radially inward such that when inner shaft 400 is advanced within inner shaft detent assembly 700 along axis C-C, inner shaft detent ball 720 is forced radially outward, further compressing inner shaft detent spring 730, and then causing inner shaft detent ball 720 to extend radially inward and engage first shank portion 405 of inner shaft 400. By engaging first shank portion 405, inner shaft 400 is locked into position such that an external force is required to remove inner shaft 400 from inner shaft detent assembly 700, and therefore knob assembly 100.

In one non-limiting embodiment, inner shaft detent cage 710 includes chamfer 710a on the proximal and distal ends of longitudinal bore 711, on the proximal and distal ends of the outer surface of inner shaft detent cage 710.

Figure 11:
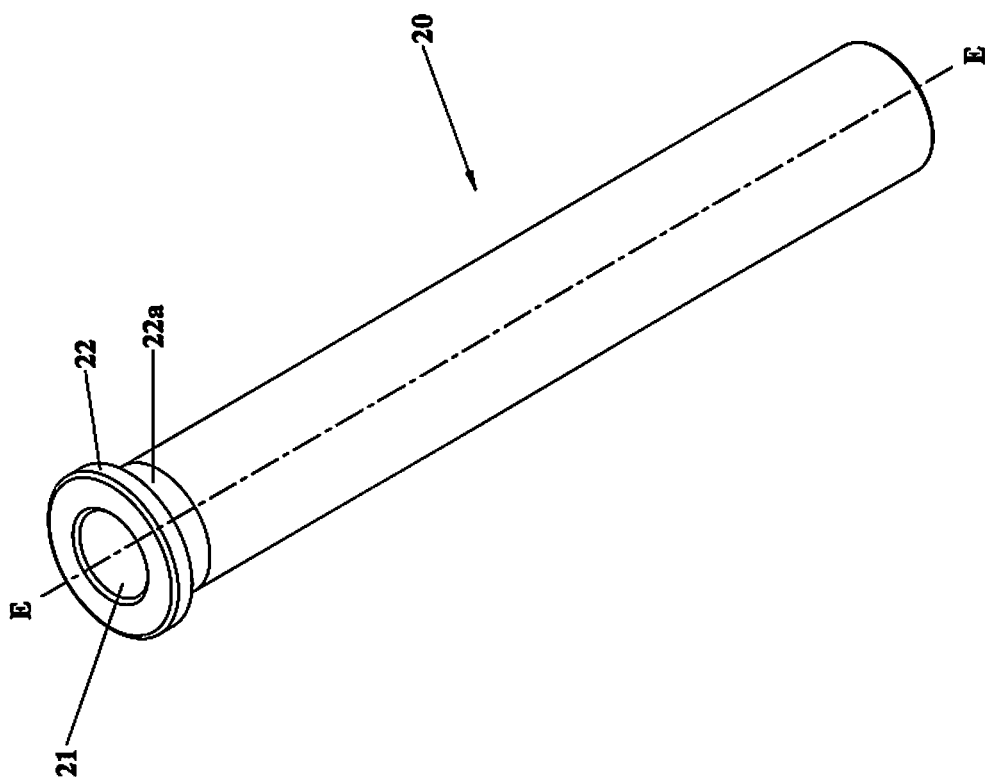
FIG. 11 is a perspective view of the handle sleeve.
Figure 12:
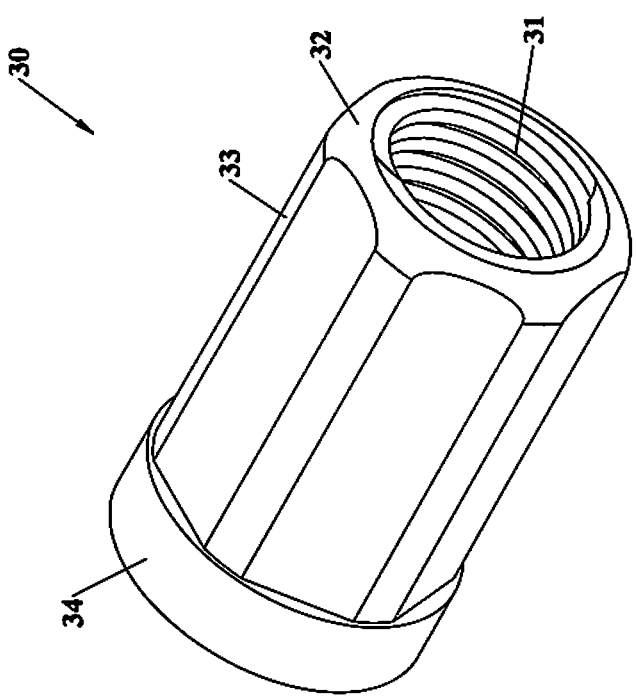
FIG. 12 is a perspective view of the handle sleeve nut.

Now referring to FIGS. 10A-11, handle sleeve 20 includes proximal and distal ends defining axis E-E. Longitudinal bore 21 extends along axis E-E and through the proximal and distal ends of handle sleeve 20. The distal end of handle sleeve 20 includes counter bore 24 (FIG. 10B). Counterbore 24 extends proximally along axis E-E and terminates with face 24b. The entrance to counter bore 24 includes chamfer 24a. Handle sleeve 20 may include boss 22 having taper 22a tapering from the larger diameter of boss 22 to the smaller diameter of the outer surface of handle sleeve 20. Handle sleeve 20 is advanced over knob assembly 100 such that boss 22 abuts handle 300, thereby preventing handle 300 from translating distally along axis C-C once handle sleeve nut 30 is secured thereto.

Figure 13:
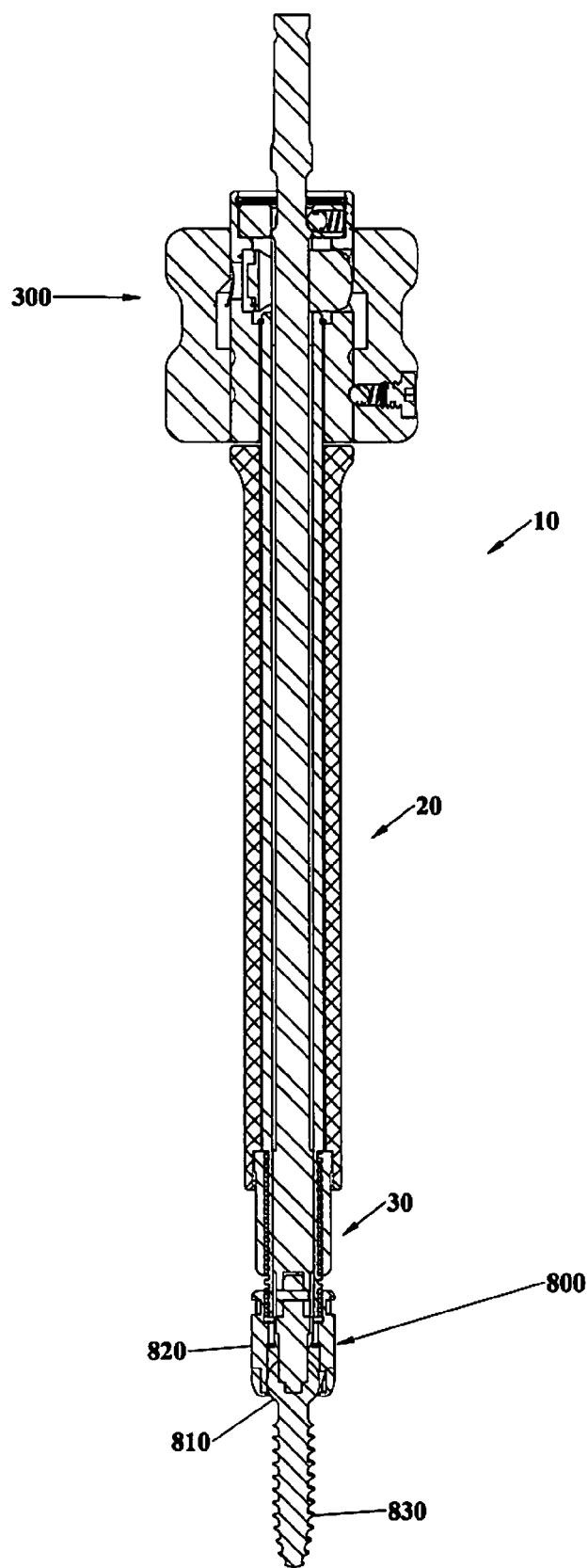
FIG. 13 is a side view of the screw insertion instrument of FIG. 1 coupled with a pedicle screw with the knob in a second position.

FIGS. 10A, 10B and 13 illustrate an embodiment of handle sleeve nut 30. Handle sleeve nut 30 has proximal and distal ends defining threaded longitudinal bore 31. Threaded longitudinal bore 31 extends through the proximal and distal ends of handle sleeve nut 30. Outer surface 33 is of hexagonal cross section such that the width of outer surface 33 is less than the diameter of counterbore 24 of handle sleeve 20. The proximal end of handle sleeve nut 30 includes circular flange 34. Circular flange 34 includes a diameter less than that of counterbore 24 of handle sleeve 20 such that handle sleeve nut 30 may abut face 24b of counterbore 24, thereby positively locating handle sleeve 20 and knob 300.

Figure 13C:
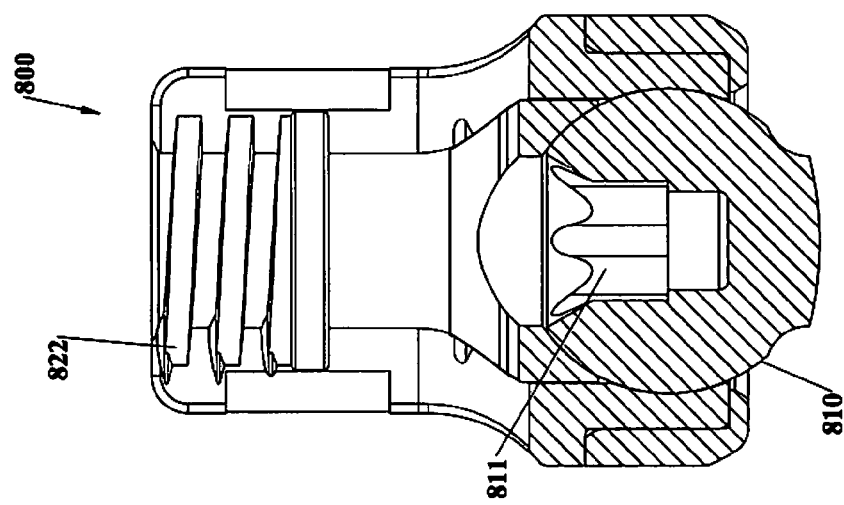
FIG. 13C is an enlarged view of the area of detail of FIG. 13B.
Figure 13B:
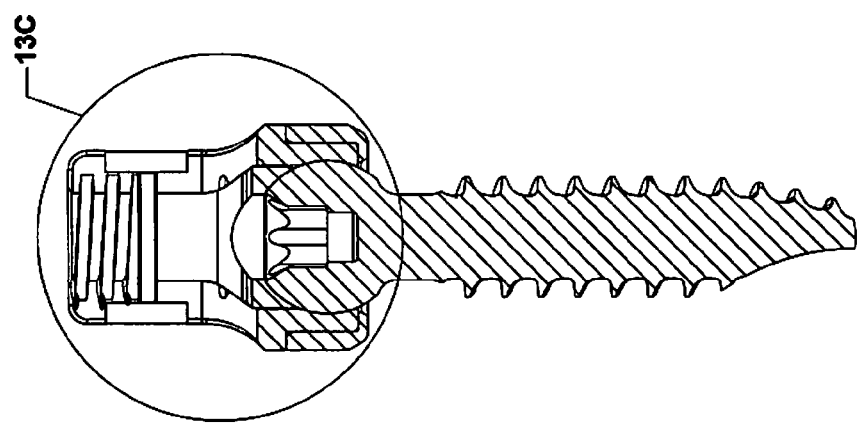
FIG. 13B is a cross-sectional view of the pedicle screw of FIG. 13A taken along section line 13B-13B.
Figure 13A:
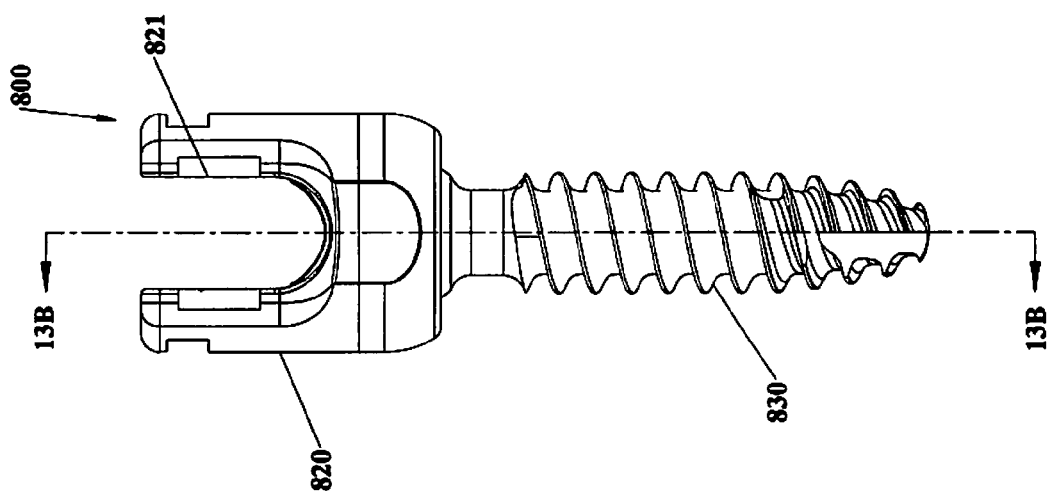
FIG. 13A is a side view of the pedicle screw of FIG. 13.

FIGS. 13A-C illustrate pedicle screw 800. Pedicle screw 800 includes a coupling element or tulip 820, a head 810 and a threaded shank 830 extending therefrom. The tulip 820 has proximal and distal ends and includes a slot 821 passing normal to the longitudinal axis of the tulip 820. The proximal end of the slot 821 includes internal threads 822 and the distal end supports the head 810 such that the head 810 may rotate or pivot with respect to the longitudinal axis of the tulip 820 but not translate with respect to the tulip 820 (i.e. the head 810 and threaded shank 830 may be polyaxial to the longitudinal axis of the tulip 820). The head 810 has a proximal end and a distal end and may be a spheroid. The proximal end of the head 810 includes a proximal portion 811 configured to engage a suitable driver, such as the screw insertion instrument 10 disclosed herein. The proximal portion 811 may be of the shape of any means known in the art to transmit the rotational motion of a driver to the head 810.

For a detailed discussion of the construction of pedicle screw 800, reference may be made to U.S. Patent Publication No. 2013/0013003, filed on Sep. 26, 2012, entitled "Polyaxial Bonescrew Assembly," the entire contents of which are incorporated herein by reference.

In operation, a clinician employs screw insertion instrument 10 to lock to a pedicle screw 800 in anticipation of securing the pedicle screw 800 in a vertebral body VB (see FIG. 13). Initially, the clinician ensures knob 300 is in a first position as shown in FIG. 1. If knob 300 is not in a first position, the clinician can advance knob 300 proximally with one hand while securing handle sleeve 20 with the other such that knob 300 may advance independent of handle sleeve 20 and lock into place by means of detent assembly 500 within second groove 209. While in this first position, knob assembly 100 is decoupled from inner shaft 400 such that knob assembly 100 may rotate with respect to inner shaft 400 about axis A-A. The clinician may next insert threaded tip 111 of support shaft 110 into a tulip 820 of a pedicle screw 800. Screw insertion instrument 10 may then be rotated around axis A-A such that threaded tip 111 is advanced within the tulip 820 of the pedicle screw 800 until the distal tip 412 of inner shaft 400 is fully seated within the head 810 of the pedicle screw 800.

Figure 14:
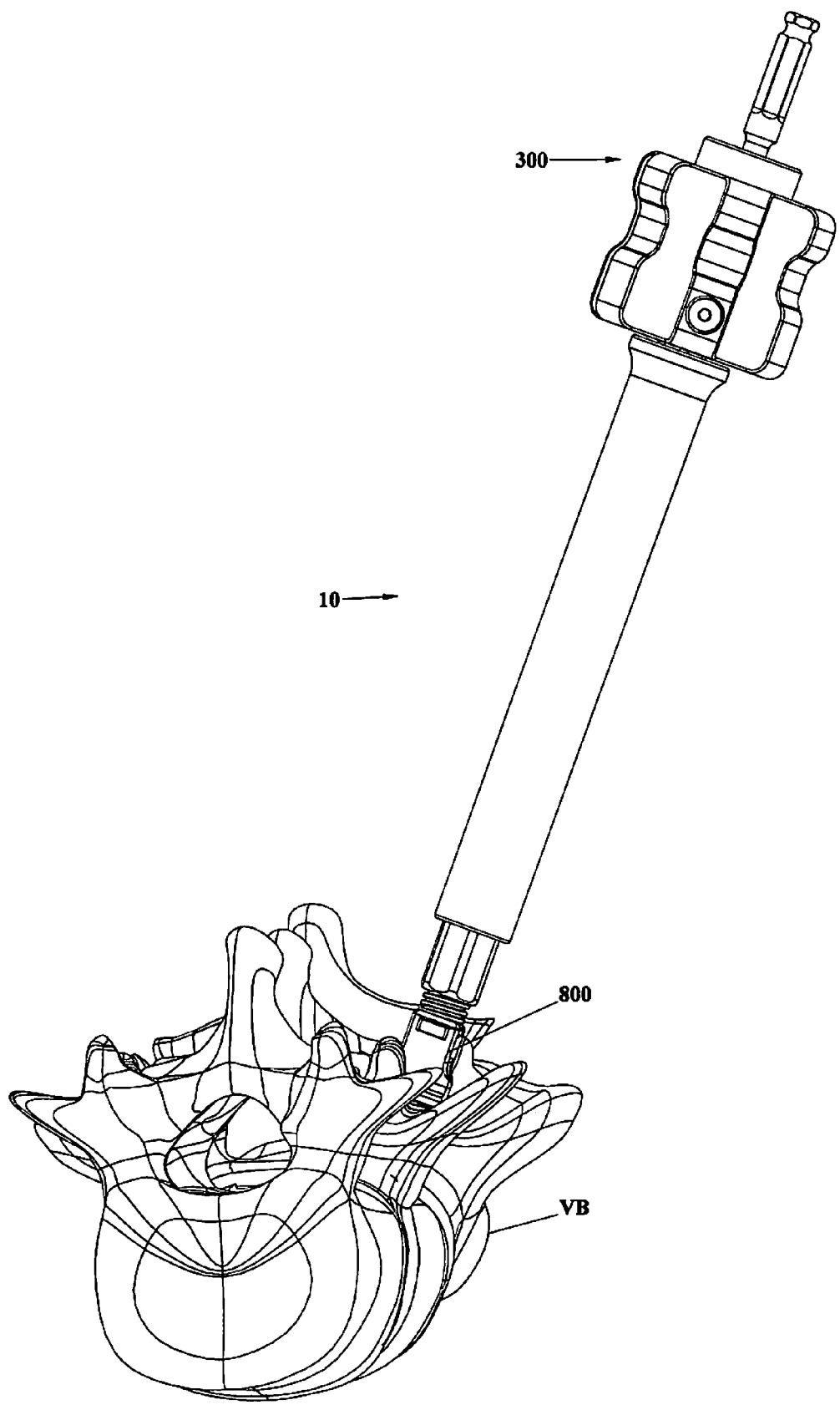
FIG. 14 is a perspective view of the screw insertion instrument of FIG. 1 coupled with a pedicle screw, wherein the screw insertion instrument of FIG. 1 is in a locked position.

The clinician may next advance knob 300 distally along axis A-A until knob 300 is locked by detent assembly 500 within first groove 208 as shown in FIG. 13. While in this second position, screw insertion instrument 10 is in mechanical engagement with inner shaft 400, such that screw insertion instrument 10 may not be disengaged from the pedicle screw. As such, screw instrument 10 and the pedicle screw 800 are "locked" together affording the clinician better control over the placement of the pedicle screw 800 within the vertebral body VB. Once the pedicle screw 800 is properly located by the clinician, the clinician may rotate screw insertion instrument 10 thereby advancing the pedicle screw 800 into a vertebral body VB and securing it thereto as shown in FIG. 14.

Figure 15:
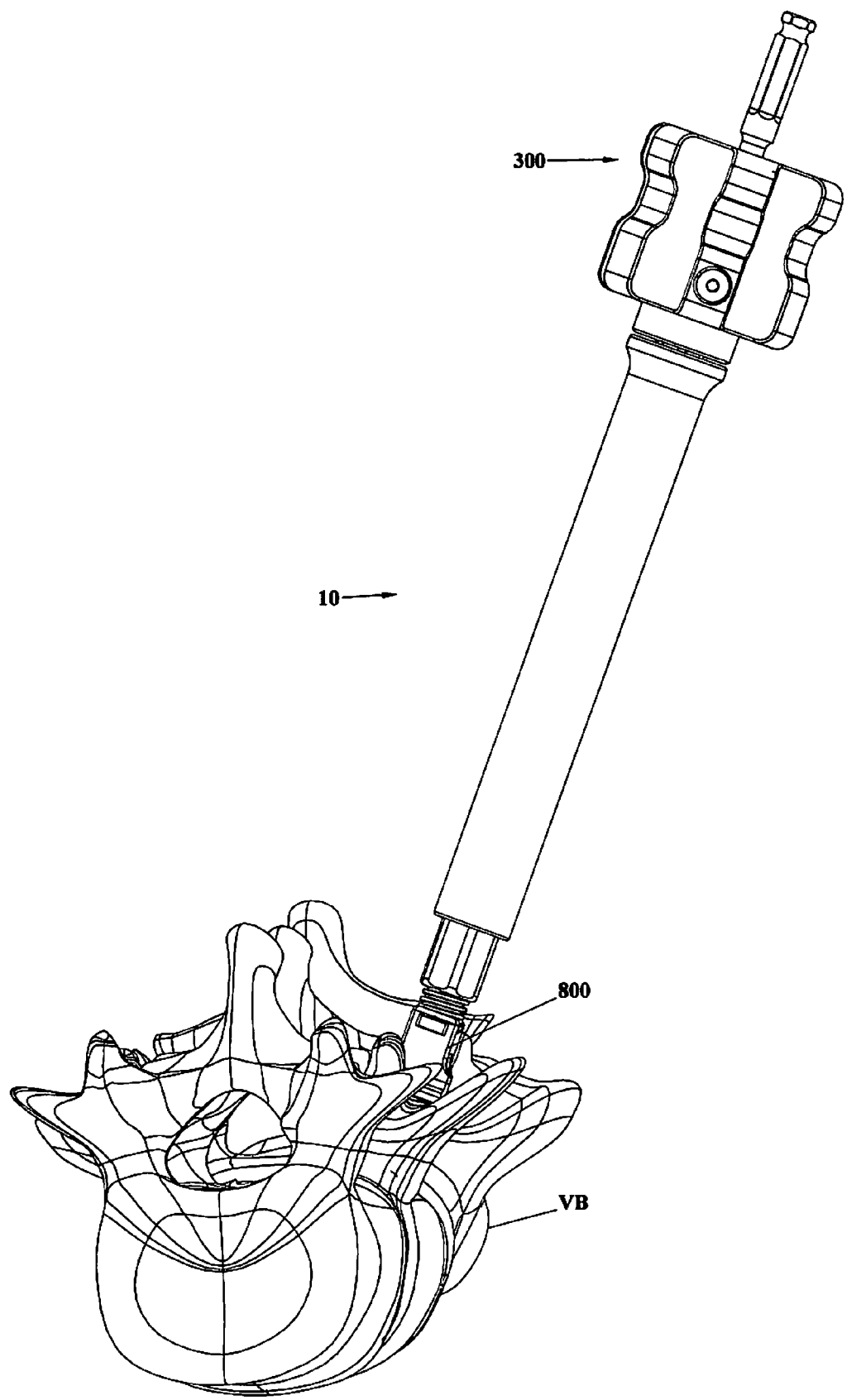
FIG. 15 is a perspective view of the screw insertion instrument of FIG. 1 coupled with a pedicle screw, wherein the screw insertion instrument of FIG. 1 is in an unlocked position.

Next, the clinician may advance knob 300 to a first position, thereby decoupling screw insertion instrument 10 from inner shaft 400 as shown in FIG. 15. In this first position, the clinician may rotate screw insertion instrument 10 such that knob assembly 100 rotates with respect to inner shaft 400 allowing screw insertion instrument 10 to be unthreaded from the tulip 820 of the pedicle screw 800 without backing out the pedicle screw 800 from the vertebral body VB.

This process may be repeated as many times as the clinician requires, whether it be for the same pedicle screw 800 or for a plurality of pedicle screw 800 as required by the procedure being performed.

It will be understood that various modifications may be made to the embodiments of the presently disclosed screw insertion instrument. Therefore, the above description should not be construed as limiting, but merely as exemplifications of embodiments. Those skilled in the art will envision other modifications within the scope and spirit of the present disclosure.

What is claimed is:

1. An insertion instrument, comprising:
    an inner shaft having an elongate body with proximal and distal ends, the distal end of the inner shaft having a tip configured to engage a pedicle screw; and
    a knob assembly, including:
        a tubular body having proximal and distal ends defining a first longitudinal bore, the first longitudinal bore adapted to rotatably and translatably support the inner shaft, wherein the distal end of the tubular body is configured to engage a tulip of the pedicle screw; and
        a knob having proximal and distal ends, the knob defining a second longitudinal bore, the second longitudinal bore configured to be slidably and non-rotatably supported by the proximal end of the tubular body, wherein the knob is selectively engageable with the inner shaft,
    wherein the inner shaft extends through and proximally from a proximal surface defined on the proximal end of the knob.

2. The instrument of claim 1, further including a handle sleeve defining a third longitudinal bore adapted to receive the tubular body.

3. The instrument of claim 2, further including a nut having an inner surface, the inner surface configured to be in mechanical cooperation with distal end of the tubular body.

4. The instrument of claim 1, wherein the inner shaft defines a longitudinal axis that extends between the proximal and distal ends of the inner shaft, the proximal end of the inner shaft including a first set of splines along the longitudinal axis.

5. The instrument of claim 4, wherein the proximal end of the second longitudinal bore of the knob includes a second set of splines to engage the first set of splines of the inner shaft.

6. The instrument of claim 5, wherein the distal end of the second longitudinal bore of the knob includes a hexagonal cross section therethrough.

7. The instrument of claim 6, wherein the proximal end of the tubular body includes a hexagonal cross section extending distally along a longitudinal axis defined by the first longitudinal bore to be engaged by the hexagonal cross section of the knob.

8. The instrument of claim 1, wherein the proximal and distal ends of the elongate body defines a longitudinal axis therethrough, wherein the knob includes a detent assembly for selectively locking the knob in a first or a second position along the longitudinal axis.

9. The instrument of claim 8, wherein the knob includes a through hole, having proximal and distal ends, extending radially inward from an outer surface of the knob towards the second longitudinal bore, wherein the through hole is configured to receive the detent assembly, wherein the distal end of the through hole is configured to prevent the detent assembly from advancing entirely therethrough.

10. The instrument of claim 9, wherein the proximal end of the tubular body includes at least two circumferential grooves, wherein the at least two circumferential grooves are configured to engage the detent assembly, wherein the at least two circumferential grooves are longitudinally spaced such that the knob may be selectively locked by one of the at least two circumferential grooves by the detent assembly.

11. The instrument of claim 9, wherein the detent assembly includes:
    a detent ball, wherein the detent ball is configured to be received by the through hole but not advance entirely therethrough,
    a detent set screw, including a head and a threaded shank extending distally therefrom, wherein the detent set screw is configured to engage the through hole; and
    a detent spring having proximal and distal ends, wherein the detent spring is disposed within the through hole and between the detent ball and the detent set screw, wherein the detent spring includes a length configured to be compressed between the detent set screw and the detent ball thereby providing a positive force upon the detent ball.

12. The instrument of claim 1, wherein the knob includes a crenellated outer surface.

13. A method for coupling an insertion instrument to a pedicle screw, the method comprising:
providing an insertion instrument having:
an inner shaft having a tip configured to engage a pedicle screw; and
a knob assembly including a distal end having a uniform circumferential profile with threads disposed thereon, the distal end of the knob assembly configured to threadably engage a tulip of the pedicle screw, wherein a proximal end of the knob assembly supports a knob, wherein the knob is selectively engageable with the inner shaft, the inner shaft extending through and proximally from a proximal surface defined on a proximal end of the knob;
inserting the tip of the inner shaft into a head of the pedicle screw;
threading the knob assembly into the tulip of the pedicle screw; and
advancing the knob distally such that the knob is in mechanical cooperation with the inner shaft.

14. The method of claim 13, wherein the method for selectively locking a screw insertion instrument to a pedicle screw includes advancing a handle sleeve over the knob assembly.

15. The method of claim 14, further including securing a nut to the knob assembly such that the handle sleeve is rotatably and translatably supported by the knob assembly.

16. The method of claim 15, further including advancing the knob assembly over the inner shaft.

17. The method of claim 16, wherein the insertion instrument further includes a longitudinal axis extending between a proximal end and a distal end of the inner shaft, the proximal end of the inner shaft including a first set of splines along the longitudinal axis, and a second set of splines is disposed within a longitudinal bore of the knob, wherein distal advancement of the knob results in engagement between the first and second sets of splines.

18. The method of claim 17, wherein the insertion instrument further includes the distal end of the longitudinal bore having a hexagonal cross section, and an outer surface of the tubular body includes a hexagonal cross section to be engaged by the hexagonal cross section of the knob, wherein rotation of the knob causes rotation of the tubular body causing the knob assembly to thread into the tulip of the pedicle screw.

19. The insertion instrument of claim 1, wherein the distal end of the tubular body is configured to threadably engage the tulip of the pedicle screw.

20. An insertion instrument, comprising:
an inner shaft having an elongate body with proximal and distal ends, the distal end of the inner shaft having a tip configured to engage a pedicle screw; and
a knob assembly, including:
a tubular body having proximal and distal ends defining a first longitudinal bore, the first longitudinal bore adapted to rotatably and translatably support the inner shaft, wherein the distal end of the tubular body is configured to engage a tulip of the pedicle screw; and
a knob having proximal and distal ends, the knob defining a second longitudinal bore, the second longitudinal bore configured to be slidably and non-rotatably supported by the proximal end of the tubular body, wherein the knob is selectively engageable with the inner shaft, wherein the proximal end of the inner shaft extends through a proximal opening of the second longitudinal bore and extends proximally from the knob and remains longitudinally stationary as the knob engages or disengages the inner shaft.

* * * * *